United States Patent
Paris et al.

(10) Patent No.: US 10,968,485 B2
(45) Date of Patent: Apr. 6, 2021

(54) DETERMINING RISK OF PROSTATE TUMOR AGGRESSIVENESS

(71) Applicant: The Regents of the University of California, Oakland, CA (US)

(72) Inventors: Pamela Paris, San Francisco, CA (US); Matthew Cooperberg, San Francisco, CA (US); Peter Carroll, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 644 days.

(21) Appl. No.: 15/455,905

(22) Filed: Mar. 10, 2017

(65) Prior Publication Data
US 2017/0183744 A1 Jun. 29, 2017

Related U.S. Application Data

(63) Continuation-in-part of application No. PCT/US2016/033753, filed on May 23, 2016.

(60) Provisional application No. 62/165,647, filed on May 22, 2015.

(51) Int. Cl.
| | |
|---|---|
| *C12Q 1/68* | (2018.01) |
| *C12P 19/34* | (2006.01) |
| *C12Q 1/6886* | (2018.01) |
| *G16B 30/00* | (2019.01) |
| *G16H 50/30* | (2018.01) |

(52) U.S. Cl.
CPC .......... *C12Q 1/6886* (2013.01); *G16B 30/00* (2019.02); *G16H 50/30* (2018.01); *C12Q 2600/106* (2013.01); *C12Q 2600/118* (2013.01); *C12Q 2600/156* (2013.01); *C12Q 2600/158* (2013.01)

(58) Field of Classification Search
CPC ............ C12Q 1/6886; C12Q 2600/106; C12Q 2600/118; C12Q 2600/156; G16H 50/30
See application file for complete search history.

(56) References Cited

U.S. PATENT DOCUMENTS

2007/0207478 A1   9/2007   Paris et al.

FOREIGN PATENT DOCUMENTS

| WO | 2011123615 A1 | 10/2011 |
| WO | 2016191358 A1 | 12/2016 |

OTHER PUBLICATIONS

GeneLoc output for Chromosome 8: Mb range of cytogenetic bands. from genecards.weizmann.ac.il, pp. 1-2, printed on Oct. 3, 2019 (Year: 2019).*
5 printed pages of Supplementary Data from Paris P.L. et al. Hum Mol Genet. Jul. 1, 2004;13(13):1303-13 (Year: 2004).*
6 printed pages of Supplementary data from Levin et al. Cancer Epidemiol Biomarkers Prev; 23(8) August (Year: 2014).*
EP16800594.0 , "Extended European Search Report", dated Nov. 14, 2018, 9 pages.
Cooperberg et al., "The CAPRA-S score: a straightforward tool for improved prediction of outcomes after radical prostatectomy," Cancer (Nov. 15, 2011) 117(22):5039-5049.
Kattan et al., "The Addition of Interleukin-6 Soluble Receptor and Transforming Growth Factor Beta$_1$ Improves a Preoperative Nomogram for Predicting Biochemical Progression in Patients With Clinically Localized Prostate Cancer," Journal of Clinical Oncology (Oct. 1, 2003) 21(19)3573-3579.
Kattan, Michael W., "Evaluating a Marker's Contribution to a Nomogram: The GEMCaP Example," Clin Cancer Res (Jan. 1, 2010) 16(1):1-3.
Levin et al., "Performance of the Genomic Evaluators of Metastatic Prostate Cancer (GEMCaP) Tumor Biomarker for Identifying Recurrent Disease in African American Patients," Cancer Epidemiol Biomarkers Prev (Aug. 2014, Published OnlineFirst Jun. 2, 2014), 23(8):1677-1682.
Paris et al., "High-Resolution Analysis of Paraffin-Embedded and Formalin-Fixed Prostate Tumors Using Comparative Genomic Hybridization to Genomic Microarrays," American Journal of Pathology (Mar. 2003) 162(3)763-770.
Paris et al., "Whole genome scanning identifies genotypes associated with recurrence and metastasis in prostate tumors," Human Molecular Genetics (2004) 13(13):1303-1313.
Paris et al., "Preliminary evaluation of prostate cancer metastatic risk biomarkers," The International Journal of Biological Markers (2005) 20(3):141-145.
Paris et al., "High Resolution Oligonucleotide CGH Using DNA From Archived Prostate Tissue," The Prostate (2007) 67:1447-1455.
Paris et al., "A Group of Genome-Based Biomarkers That Add to a Kattan Nomogram for Predicting Progression in Men with High-Risk Prostate Cancer," Clin Cancer Res (Jan. 1, 2010) 16(1):195-202.
Shariat et al., "External Validation of a Biomarker-Based Preoperative Nomogram Predicts Biochemical recurrence After Radical Prostatectomy," Amer Soc Clin Oncol (Mar. 20, 2008) 26(9):1526-1531.
PCT/US2016/033753 , "International Search Report and Written Opinion", dated Aug. 26, 2016, 14 pages.

* cited by examiner

*Primary Examiner* — Stephen T Kapushoc
(74) *Attorney, Agent, or Firm* — Kilpatrick Townsend & Stockton LLP

(57) ABSTRACT

This disclosure relates to methods, computer products, computer-implemented methods, and systems for predicting the probability or risk of prostate cancer recurrence and tumor aggressiveness in a patient. The method is based, in part, on the patient's risk profile that includes the presence/degree of specific copy number variations and predictive clinical factors. The methods and systems can be used to aid in treatment selection.

8 Claims, 1 Drawing Sheet

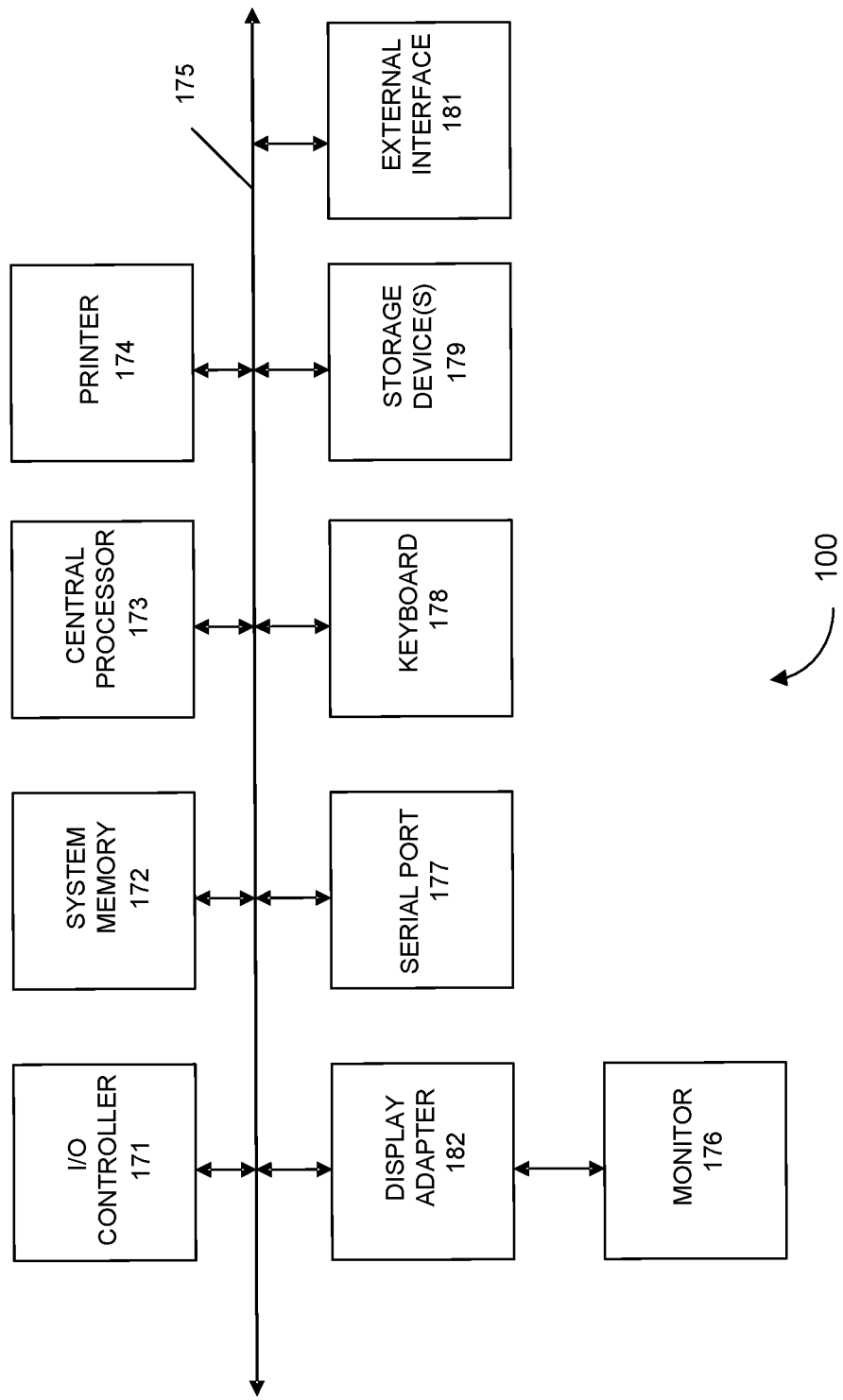

DETERMINING RISK OF PROSTATE TUMOR AGGRESSIVENESS

CROSS-REFERENCE TO RELATED APPLICATIONS

This application is a continuation-in-part of PCT Patent Application No. PCT/US2016/033753, filed May 23, 2016, which claims benefit of priority to U.S. Provisional Patent Application No. 62/165,647, filed May 22, 2015. The contents of each application is hereby incorporated by reference in its entirety for all purposes.

STATEMENT AS TO RIGHTS TO INVENTIONS MADE UNDER FEDERALLY SPONSORED RESEARCH AND DEVELOPMENT

This invention was made with government support under Grant No. W81XWH-11-1-0489 awarded by the United States Army Medical Research and Materiel Command. The government has certain rights in the invention.

BACKGROUND OF THE INVENTION

Prostate cancer is the most common cancer diagnosis and the second most common cause of cancer related deaths in men. Diagnosing and managing prostate cancer are clinically difficult due to lack of the knowledge of the cancer at molecular and genetic levels and a lack of understanding of the natural disease progression. Currently, serum prostate-specific antigen (PSA) is the only biomarker widely used in the diagnosis and management of patients. PSA lacks diagnostic sensitivity and specificity, leading to false-negative and false-positive test results. Several preoperative classification systems have been developed. For example, Kaftan nonograms (U.S. Pat. Nos. 5,993,388 and 6,409,664), the D'Amico classification, and the Cancer of the Prostate Risk Assessment (CAPRA) score each incorporate the measurement of several pre-operative clinical markers to determine the probability of prostate cancer.

Treatment of clinically localized prostate cancer is typically radical prostatectomy. Unfortunately, following surgery many men experience an increase in serum PSA, cancer recurrence or progression of the disease months or years later. The ability to identify, or predict, a post-surgery patient as likely to encounter PSA failure, recurrence of the prostate cancer, and/or development of metastasis, would provide multiple benefits to the patient.

BRIEF SUMMARY OF THE INVENTION

In one aspect, provided herein is a method for determining a risk of prostate cancer recurrence in a human subject. The method includes: (a) detecting a set of copy numbers for a set of genomic regions or portions thereof in a biological sample obtained from the subject; (b) scoring each genomic region or portion thereof as diseased or normal, wherein the scoring is determined based on the copy number of the biological sample compared to a reference copy number; (c) comparing the number of diseased genomic regions from step (b) to a threshold value for disease recurrence to generate a copy number score; (d) calculating a clinical score comprising one or more factors selected from the group consisting of a preoperative or postoperative prostate-specific antigen (PSA) level, pathogenic Gleason score, surgical margin status, presence of extracapsular extension, presence of seminal vesicle, and presence of lymph node involvement, wherein each factor is assigned a numerical value; and (e) predicting a risk of prostate cancer recurrence for the subject based on the copy number score and the clinical score. In some cases, the clinical score also includes the subject's age.

In some embodiments, the set of genomic regions or portions thereof comprises genomic regions or portions thereof at human chromosomes 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 and 16q23.1. In some instances, the genomic region or portion thereof is scored as diseased if there is an increase in copy number at the genomic region or portion thereof at human chromosome 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, or 22q13.1 in the biological sample compared to the reference copy number, and if there is a decrease in copy number at the genomic region or portion thereof at human chromosome 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 or 16q23.1 in the biological sample compared to the reference copy number. In some cases, the clinical score comprises the numerical values assigned to the preoperative or postoperative prostate-specific antigen (PSA) level, the pathogenic Gleason score, the surgical margin status, the presence of extracapsular extension, the presence of seminal vesicle, and the presence of lymph node involvement.

The genomic region or portion thereof at human chromosome 3q26.2 can comprise a genomic region or portion thereof at chr3:168805847-168806351, the genomic region or portion thereof at human chromosome 3q26.32 can comprise a genomic region or portion thereof at chr3:177272862-177430308, the genomic region or portion thereof at human chromosome 3q26.3 can comprise a genomic region or portion thereof at chr3:178951957-178952231, the genomic region or portion thereof at human chromosome 5p15.1 can comprise a genomic region or portion thereof at chr5:17412420-17592769, the genomic region or portion thereof at human chromosome 7p22.3 can comprise one or more genomic regions or portions thereof at chr7:1062717-1063110 and/or chr7:2396631-2396986, the genomic region or portion thereof at human chromosome 7q11.22 can comprise a genomic region or portion thereof at chr7:69577003-69759243, the genomic region or portion thereof at human chromosome 7q11.23 can comprise a genomic region or portion thereof at chr7:73442517-73483030, the genomic region or portion thereof at human chromosome 7q22.1 can comprise a genomic region or portion thereof at chr7:100705095-100899914, the genomic region or portion thereof at human chromosome 7q31.31 can comprise a genomic region or portion thereof at chr7:117432355-117432817, the genomic region or portion thereof at human chromosome 9q34.1 can comprise a genomic region or portion thereof at chr9:132262446-132370055, the genomic region or portion thereof at human chromosome 11p15.4 can comprise a genomic region or portion thereof at chr11:2904813-2907001, 17q21.33 can comprise a genomic region or portion thereof at chr17:47454237-47654582, the genomic region or portion thereof at human chromosome 17q25.3 can comprise a genomic region or portion thereof at chr17:77702278-77862768, the genomic region or portion thereof at human chromosome 22q13.1 can comprise a genomic region or portion thereof at chr22:39620241-39631867, the genomic region or portion thereof at human chromosome 4p13 can comprise a genomic region or portion thereof at chr4:44558370-44559188, the genomic region or portion thereof at human chromosome 5q13.1 can comprise a genomic region or portion thereof at chr5:67803220-67803609, the genomic region or portion thereof at human chromosome 5q14.3 can comprise a genomic region or portion thereof at chr5:85936281-86082787, the genomic region or portion thereof at human chromosome 5q21.1 can comprise a genomic region or portion thereof at chr5:102652546-102813426, the genomic region or portion thereof at human chromosome 5q21.2 can comprise a genomic region or portion thereof at chr5:103047961-103230737, the genomic region or portion thereof at human chromosome 5q21.3 can comprise a genomic region or portion thereof at chr5:108476063-108523316, the genomic region or portion thereof at human chromosome 5q23.1 can comprise a genomic region or portion thereof at chr5:116987516-116987850, at the genomic region or portion thereof human chromosome 6q14.1 can comprise a genomic region or portion thereof at chr6:79240539-79417494, the genomic region or portion thereof at human chromosome 6q21 can comprise one or more genomic regions or portions thereof at chr6:105514625-105687735 and/or chr6:112401839-112550863, the genomic region or portion thereof at human chromosome 8p22 can comprise a genomic region or portion thereof at chr8:15649576-15649945, the genomic region or portion thereof at human chromosome 8p21.2 can comprise one or more genomic regions or portions thereof at chr8:25189716-25280826, chr8:26260492-26362544, and/or chr8:26555762-26676439, the genomic region or portion thereof at human chromosome 8p12 can comprise a genomic region or portion thereof at chr8:32412399-32572832, the genomic region or portion thereof at human chromosome 10q23.31 can comprise a genomic region or portion thereof at chr10:89991491-90075908, the genomic region or portion thereof at human chromosome 13q14.11 can comprise one or more genomic regions or portions thereof at chr13:40129477-40205232, chr13:41044273-41044745, and/or chr13:43679675-43868415, the genomic region or portion thereof at human chromosome 13q14.13 can comprise a genomic region or portion thereof at chr13:45857696-45858096, the genomic region or portion thereof at human chromosome 13q14.2 can comprise a genomic region or portion thereof at chr13:49015662-49140264, the genomic region or portion thereof at human chromosome 13q14.3 can comprise a genomic region or portion thereof at chr13:51245126-51245378 and the genomic region or portion thereof at human chromosome 16q23.1 can comprise a genomic region or portion thereof at chr16:77158148-77311367. Specific genomic regions or portions thereof that are located at human chromosomes 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 and 16q23.1 are provided in Table 1.

A portion of a genomic region can include, for example, 10-1,000 consecutive nucleotides; 100-1,000 consecutive nucleotides; 10-10,000 consecutive nucleotides; 10-300,000 consecutive nucleotides; 10-100,000 consecutive nucleotides; 100-300,000 consecutive nucleotides; 1,000-300,000 consecutive nucleotides; 1,000-100,000 consecutive nucleotides; 10,000-300,000 consecutive nucleotides; 100,000-300,000 consecutive nucleotides; or more.

In some embodiments, the set of genomic regions or portions thereof comprises one or more, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 genomic regions or portions thereof selected from the group consisting of human chromosome(s) 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 and 16q23.1. In some cases, the genomic region or portion thereof is scored as diseased if there is an increase in copy number at the genomic region or portion thereof located at human chromosome 3q26.2, 3q26.32, 3q26.3, 5p15.1, 7p22.3, 7811.22, 7811.23, 7822.1, 7831.31, 9834.1, 11p15.4, 17q21.33, 17825.3, or 22813.1 in the biological sample compared to the reference copy number, and if there is a decrease in copy number at the genomic region or portion thereof located at human chromosome 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 or 16q23.1 in the biological sample compared to the reference copy number.

In other embodiments, the set of genomic regions or portions thereof comprises the genomic regions or portions thereof located at human chromosomes 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 and 16q23.1, wherein the genomic region or portion thereof is scored as diseased if there is an increase in copy number at the genomic region or portion thereof located at human chromosome 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, or 22q13.1 in the biological sample compared to the reference copy number, and if there is a decrease in copy number at the genomic region or portion thereof located at human chromosome 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 or 16q23.1 in the biological sample compared to reference copy number.

In some embodiments, the clinical score comprises the numerical values assigned to the prostate-specific antigen (PSA) level, the pathogenic Gleason score, the surgical margin status, the presence of extracapsular extension, the presence of seminal vesicle, and the presence of lymph node involvement.

The threshold value for disease recurrence can correspond to at least 10%, e.g., 10%, 11%, 12%, 13%, 14%, 15%, 16%, 17%, 18%, 19%, 20%, or more of the set of genomic regions or portions thereof are scored as diseased. Also, the threshold value for disease recurrence can correspond to at least 15%, e.g., 15%, 16%, 17%, 18%, 19%, 20%, or more of the set of genomic regions or portions thereof are scored as diseased. In other cases, the threshold value for disease recurrence can correspond to at least 20%, e.g., 20%, 21%, 22%, 23%, 24%, 25%, 26%, 27%, 28%, 29%, 30%, 31%, 32%, 33%, 34%, 35%, 36%, 37%, 38%, 39%, 40% or more of the set of genomic regions or portions thereof are scored as diseased.

In some embodiments, the step of detecting the set of copy numbers comprises performing comparative genomic hybridization, genomic sequencing, or a genomic amplification reaction assay.

In some embodiments, the subject has had surgery to remove prostate cancer tissue. The surgery can be radical prostatectomy. The biological sample can be selected from a prostate cancer tissue sample, a circulating tumor cell sample, a metastatic tissue sample, a lymph node sample, a prostate tissue sample, a blood sample, a serum sample, a plasma sample, and a combination thereof. The biological sample can be a postoperative sample.

The method described herein can also include treating the subject having a risk of prostate cancer recurrence with a therapy to kill, inhibit, or remove prostate cancer cells. Alternatively, the method can include committing the subject to active surveillance if the subject does not have a risk of prostate cancer recurrence.

In another aspect, provided herein is a method for detecting a set of copy numbers in a set of genomic regions or portions thereof and clinical factors in a subject having a risk of prostate cancer recurrence. The method includes (a) obtaining a biological sample from the subject; (b) detecting the set of copy numbers for the set of genomic regions or portions thereof in the biological sample; (c) measuring the level of PSA in a sample from the subject; and (d) performing one or more clinical assays selected from the group consisting of a pathogenic Gleason score assay, a surgical margin status assay, an extracapsular extension assay, a seminal vesicle assay, and a lymph node involvement assay.

In some embodiments, the set of genomic regions or portions thereof comprises one or more e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 genomic regions or portions thereof selected from the group consisting of human chromosome(s) 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 and 16q23.1.

In other embodiments, the set of genomic regions or portions comprises the genomic regions or portions thereof at human chromosomes 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 and 16q23.1.

The genomic region or portion thereof at human chromosome 3q26.2 can comprise a genomic region or portion thereof at chr3:168805847-168806351, the genomic region or portion thereof at human chromosome 3q26.32 can comprise a genomic region or portion thereof at chr3:177272862-177430308, the genomic region or portion thereof at human chromosome 3q26.3 can comprise a genomic region or portion thereof at chr3:178951957-178952231, the genomic region or portion thereof at human chromosome 5p15.1 can comprise a genomic region or portion thereof at chr5:17412420-17592769, the genomic region or portion thereof at human chromosome 7p22.3 can comprise one or more genomic region(s) or portion(s) thereof at chr7:1062717-1063110 and/or chr7:2396631-2396986, the genomic region or portion thereof at human chromosome 7q11.22 can comprise a genomic region or portion thereof at chr7:69577003-69759243, the genomic region or portion thereof at human chromosome 7q11.23 can comprise a genomic region or portion thereof at chr7:73442517-73483030, the genomic region or portion thereof at human chromosome 7q22.1 can comprise a genomic region or portion thereof at chr7:100705095-100899914, the genomic region or portion thereof at human chromosome 7q31.31 can comprise a genomic region or portion thereof at chr7:117432355-117432817, the genomic region or portion thereof at human chromosome 9q34.1 can comprise a genomic region or portion thereof at chr9:132262446-132370055, the genomic region or portion thereof at human chromosome 11p15.4 can comprise a genomic region or portion thereof at chr11:2904813-2907001, 17q21.33 can comprise a genomic region or portion thereof at chr17:47454237-47654582, the genomic region or portion thereof at human chromosome 17q25.3 can comprise a genomic region or portion thereof at chr17:77702278-77862768, the genomic region or portion thereof at human chromosome 22q13.1 can comprise a genomic region or portion thereof at chr22:39620241-39631867, the genomic region or portion thereof at human chromosome 4p13 can comprise a genomic region or portion thereof at chr4:44558370-44559188, the genomic region or portion thereof at human chromosome 5q13.1 can comprise a genomic region or portion thereof at chr5:67803220-67803609, the genomic region or portion thereof at human chromosome 5q14.3 can comprise a genomic region or portion thereof at chr5:85936281-86082787, the genomic region or portion thereof at human chromosome 5q21.1 can comprise a genomic region or portion thereof at chr5:102652546-102813426, the genomic region or portion thereof at human chromosome 5q21.2 can comprise a genomic region or portion thereof at chr5:103047961-103230737, the genomic region or portion thereof at human chromosome 5q21.3 can comprise a genomic region or portion thereof at chr5:108476063-108523316, the genomic region or portion thereof at human chromosome 5q23.1 can comprise a genomic region or portion thereof at chr5:116987516-116987850, at the genomic region or portion thereof human chromosome 6q14.1 can comprise a genomic region or portion thereof at chr6:79240539-79417494, the genomic region or portion thereof at human chromosome 6q21 can comprise one or more genomic region(s) or portion(s) thereof at chr6:105514625-105687735 and/or chr6:112401839-112550863, the genomic region or portion thereof at human chromosome 8p22 can comprise a genomic region or portion thereof at chr8:15649576-15649945, the genomic region or portion thereof at human chromosome 8p21.2 can comprise one or more genomic region(s) or portion(s) thereof at chr8:25189716-25280826, chr8:26260492-26362544, and/or chr8:26555762-26676439, the genomic region or portion thereof at human chromosome 8p12 can comprise a genomic region or portion thereof at chr8:32412399-32572832, the genomic region or portion thereof at human chromosome 10q23.31 can comprise a genomic region or portion thereof at chr10:89991491-90075908, the genomic region or portion thereof at human chromosome 13q14.11 can comprise one or more genomic region(s) or portion(s) thereof at chr13:40129477-40205232, chr13:41044273-41044745, and/or chr13:43679675-43868415, the genomic region or portion thereof at human chromosome 13q14.13 can comprise a genomic region or portion thereof at chr13:45857696-45858096, the genomic region or portion thereof at human chromosome 13q14.2 can comprise a genomic region or portion thereof at chr13:49015662-49140264, the genomic region or portion thereof at human chromosome 13q14.3 can comprise a genomic region or portion thereof at chr13:51245126-51245378 and the genomic region or portion thereof at human chromosome 16q23.1 can comprise a genomic region or portion thereof at chr16:77158148-77311367. Specific genomic regions or portions thereof that are located at human chromosomes 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 and 16q23.1 are provided in Table 1.

The step of detecting the set of copy numbers can include performing comparative genomic hybridization, genomic sequencing, or a genomic amplification reaction assay. The step of performing the one or more clinical assays can include performing a pathogenic Gleason score assay, performing a surgical margin status assay, performing an extracapsular extension assay, performing a seminal vesicle assay, and performing a lymph node involvement assay.

The biological sample of the method can be selected from a prostate cancer tissue sample, a circulating tumor cell sample, a metastatic tissue sample, a lymph node sample, a prostate tissue sample, a blood sample, a serum sample, a plasma sample, and a combination thereof. The sample for measuring the level of PSA can be a blood sample.

In another aspect, provided herein is a computer product comprising a non-transitory computer readable medium storing a plurality of instructions that when executed determine a human subject's risk of prostate cancer recurrence. The instructions include receiving a set of determined copy numbers for a set of genomic regions or portions thereof comprising one or more genomic regions or portions thereof selected from the group consisting of human chromosome(s) 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5814.3, 5821.1, 5821.2, 5821.3, 5823.1, 6814.1, 6821, 8p22, 8p21.2, 8p12, 10q23.31, 13q14.11, 13q14.13, 13q14.2, 13q14.3 and 16q23.1 in a biological sample from the subject; comparing the set of determined copy numbers to a set of reference copy numbers for the corresponding set of genomic regions or portions thereof scoring each genomic region or portion thereof as diseased or normal, wherein the genomic region or portion thereof is diseased if there is an increase in copy number at the genomic region or portion thereof at human chromosome 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, or 22813.1 in the biological sample compared to the reference copy number, and if there is a decrease in copy number at the genomic region or portion thereof at human chromosome 4p13, 5q13.1, 5 q14.3, 5q21.1, 5q21.2, 5q21.3, 5823.1, 6814.1, 6q21, 8p22, 8p21.2, 8p12, 10q23.31, 13814.11, 13q14.13, 13q14.2, 13q14.3 or 16q23.1 in the biological sample compared to the reference copy number; comparing the number of genomic regions or portions thereof that are scored as diseased to a threshold value for disease recurrence to generate a copy number score; receiving a set of determined clinical factors for the subject, the set of determined clinical factors comprising one or more clinical factors comprising a PSA level (e.g., a preoperative PSA level or a postoperative PSA level), pathogenic Gleason score, surgical margin status, presence of extracapsular extension, presence of seminal vesicle, and presence of lymph node involvement to generate a clinical score; and determining the subject's risk of prostate cancer recurrence by based on a calculation comprising the copy number score and the clinical score.

In some embodiments, the set of genomic regions or portions thereof comprises the genomic regions or portions thereof at human chromosomes 3q26.2, 3q26.32, 3q26.3, 5p15.1, 7p22.3, 7811.22, 7811.23, 7822.1, 7831.31, 9834.1, 11p15.4, 17q21.33, 17825.3, 22813.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 and 16q23.1.

The genomic region or portion thereof at human chromosome 3q26.2 can comprise a genomic region or portion thereof at chr3:168805847-168806351, the genomic region or portion thereof at human chromosome 3q26.32 can comprise a genomic region or portion thereof at chr3:177272862-177430308, the genomic region or portion thereof at human chromosome 3q26.3 can comprise a genomic region or portion thereof at chr3:178951957-178952231, the genomic region or portion thereof at human chromosome 5p15.1 can comprise a genomic region or portion thereof at chr5:17412420-17592769, the genomic region or portion thereof at human chromosome 7p22.3 can comprise one or more genomic regions or portions thereof at chr7:1062717-1063110 and/or chr7:2396631-2396986, the genomic region or portion thereof at human chromosome 7q11.22 can comprise a genomic region or portion thereof at chr7:69577003-69759243, the genomic region or portion thereof at human chromosome 7q11.23 can comprise a genomic region or portion thereof at chr7:73442517-73483030, the genomic region or portion thereof at human chromosome 7q22.1 can comprise a genomic region or portion thereof at chr7:100705095-100899914, the genomic region or portion thereof at human chromosome 7q31.31 can comprise a genomic region or portion thereof at chr7:117432355-117432817, the genomic region or portion thereof at human chromosome 9q34.1 can comprise a genomic region or portion thereof at chr9:132262446-132370055, the genomic region or portion thereof at human chromosome 11p15.4 can comprise a genomic region or portion thereof at chr11:2904813-2907001, 17q21.33 can comprise a genomic region or portion thereof at chr17:47454237-47654582, the genomic region or portion thereof at human chromosome 17q25.3 can comprise a genomic region or portion thereof at chr17:77702278-77862768, the genomic region or portion thereof at human chromosome 22q13.1 can comprise a genomic region or portion thereof at chr22:39620241-39631867, the genomic region or portion thereof at human chromosome 4p13 can comprise a genomic region or portion thereof at chr4:44558370-44559188, the genomic region or portion thereof at human chromosome 5q13.1 can comprise a genomic region or portion thereof at chr5:67803220-67803609, the genomic region or portion thereof at human chromosome 5q14.3 can comprise a genomic region or portion thereof at chr5:85936281-86082787, the genomic region or portion thereof at human chromosome 5q21.1 can comprise a genomic region or portion thereof at chr5:102652546-102813426, the genomic region or portion thereof at human chromosome 5q21.2 can comprise a genomic region or portion thereof at chr5:103047961-103230737, the genomic region or portion thereof at human chromosome 5q21.3 can comprise a genomic region or portion thereof at chr5:108476063-108523316, the genomic region or portion thereof at human chromosome 5q23.1 can comprise a genomic region or portion thereof at chr5:116987516-116987850, at the genomic region or portion thereof human chromosome 6q14.1 can comprise a genomic region or portion thereof at chr6:79240539-79417494, the genomic region or portion thereof at human chromosome 6q21 can comprise one or more genomic regions or portions thereof at chr6:105514625-105687735 and/or chr6:112401839-112550863, the genomic region or portion thereof at human chromosome 8p22 can comprise a genomic region or portion thereof at chr8:15649576-15649945, the genomic region or portion thereof at human chromosome 8p21.2 can comprise one or more genomic regions or portions thereof at chr8:25189716-25280826, chr8:26260492-26362544, and/or chr8:

26555762-26676439, the genomic region or portion thereof at human chromosome 8p12 can comprise a genomic region or portion thereof at chr8:32412399-32572832, the genomic region or portion thereof at human chromosome 10q23.31 can comprise a genomic region or portion thereof at chr10: 89991491-90075908, the genomic region or portion thereof at human chromosome 13q14.11 can comprise one or more genomic regions or portions thereof at chr13:40129477-40205232, chr13:41044273-41044745, and/or chr13:43679675-43868415, the genomic region or portion thereof at human chromosome 13q14.13 can comprise a genomic region or portion thereof at chr13:45857696-45858096, the genomic region or portion thereof at human chromosome 13q14.2 can comprise a genomic region or portion thereof at chr13:49015662-49140264, the genomic region or portion thereof at human chromosome 13q14.3 can comprise a genomic region or portion thereof at chr13:51245126-51245378 and the genomic region or portion thereof at human chromosome 16q23.1 can comprise a genomic region or portion thereof at chr16:77158148-77311367. Specific genomic regions or portions thereof that are located at human chromosomes 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 and 16q23.1 are provided in Table 1.

In some embodiments, the set of determined copy numbers is generated by performing comparative genomic hybridization, genomic sequencing, or a genomic amplification reaction assay on the biological sample.

In some embodiments, the threshold value for disease recurrence can correspond to at least 10%, e.g., 10%, 11%, 12%, 13%, 14%, 15%, 16%, 17%, 18%, 19%, 20%, or more of the set of genomic regions or portions thereof are scored as diseased. In other embodiments, the threshold value for disease recurrence can correspond to at least 15%, e.g., 15%, 16%, 17%, 18%, 19%, 20%, or more of the set of genomic regions or portions thereof are scored as diseased. In yet other embodiments, the threshold value for disease recurrence can correspond to at least 20%, e.g., 20%, 21%, 22%, 23%, 24%, 25%, 26%, 27%, 28%, 29%, 30%, 31%, 32%, 33%, 34%, 35%, 36%, 37%, 38%, 39%, 40%, or more of the set of genomic regions or portions thereof are scored as diseased.

In some instances, the set of determined clinical factors comprises the PSA level (e.g., the preoperative PSA level), the pathogenic Gleason score, the surgical margin status, the presence of extracapsular extension, the presence of seminal vesicle, and the presence of lymph node involvement.

In another aspect, provided herein is a computer-implemented method for determining a risk of prostate cancer recurrence in a subject. The method includes (a) receiving, at one or more computer system(s), information about a set of copy numbers for a set of genomic regions or portions thereof comprising one or more genomic regions or portions thereof selected from the group consisting of human chromosome(s) 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5q14.3, 5q21.1, 5q21.2, 5q21.3, 5q23.1, 6q14.1, 6821, 8p22, 8p21.2, 8p12, 10q23.31, 13q14.11, 13q14.13, 13q14.2, 13q14.3 and 16q23.1 in a biological sample obtained from the subject; (b) performing, with one or more processors associated with the computer system(s), a comparison of the set of copy numbers in the biological sample to a set of reference copy numbers to score the genomic region or portion thereof as diseased or normal, wherein the genomic region or portion thereof is diseased if there is an increase in copy number at the genomic region or portion thereof at human chromosome 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, or 22q13.1 in the biological sample compared to the reference copy number, and if there is a decrease in copy number at the genomic region or portion thereof at human chromosome 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 or 16q23.1 in the biological sample compared to the reference copy number; (c) performing, with one or more processors associated with the computer system(s), a comparison of the number of genomic regions or portions thereof that are scored as diseased to a threshold value for disease recurrence to generate a copy number score; (d) receiving, at one or more computer system(s), information about a set of clinical factors for the subject, the set of clinical factors comprising one or more of the clinical factors comprising a PSA level (e.g., a preoperative PSA level), pathogenic Gleason score, surgical margin status, presence of extracapsular extension, presence of seminal vesicle, and presence of lymph node involvement, wherein each clinical factor is assigned a numerical value; (e) generating, with one or more processors associated with the computer system(s), a clinical score based on the numerical values assigned to the set of clinical factors; and (0 generating, with one or more processors associated with the computer system(s), a determination of a risk of prostate cancer recurrence comprising the copy number score and the clinical score, and predicting a high risk of prostate cancer recurrence if the risk of prostate cancer recurrence is higher than a threshold risk score, or a low risk of prostate cancer recurrence if the risk of prostate cancer recurrence is lower than the threshold risk score.

The threshold value for disease recurrence can correspond to at least 10%, e.g., 10%, 11%, 12%, 13%, 14%, 15%, 16%, 17%, 18%, 19%, 20%, or more of the set of genomic regions or portions thereof are scored as diseased. In some cases, the threshold value for disease recurrence can correspond to at least 15%, e.g., 15%, 16%, 17%, 18%, 19%, 20%, or more of the set of genomic regions or portions thereof are scored as diseased. In other cases, the threshold value for disease recurrence can correspond to at least 20%, e.g., 20%, 21%, 22%, 23%, 24%, 25%, 26%, 27%, 28%, 29%, 30%, 31%, 32%, 33%, 34%, 35%, 36%, 37%, 38%, 39%, 40% or more of the set of genomic regions or portions thereof are scored as diseased.

In some embodiments, the set of genomic regions or portions thereof includes the genomic regions or portions thereof at human chromosomes 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 and 16q23.1.

The genomic region or portion thereof at human chromosome 3q26.2 can comprise a genomic region or portion thereof at chr3:168805847-168806351, the genomic region or portion thereof at human chromosome 3q26.32 can comprise a genomic region or portion thereof at chr3:177272862-177430308, the genomic region or portion thereof at human chromosome 3q26.3 can comprise a genomic region or portion thereof at chr3:178951957-178952231, the genomic region or portion thereof at human chromosome 5p15.1 can comprise a genomic region or portion thereof at chr5:17412420-17592769, the genomic region or portion thereof at human chromosome 7p22.3 can comprise one or more genomic regions or portions thereof at chr7:1062717-1063110 and/or chr7:2396631-2396986, the genomic region or portion thereof at human chromosome 7q11.22 can comprise a genomic region or portion thereof at chr7:69577003-69759243, the genomic region or portion thereof at human chromosome 7q11.23 can comprise a genomic region or portion thereof at chr7:73442517-73483030, the genomic region or portion thereof at human chromosome 7q22.1 can comprise a genomic region or portion thereof at chr7:100705095-100899914, the genomic region or portion thereof at human chromosome 7q31.31 can comprise a genomic region or portion thereof at chr7: 117432355-117432817, the genomic region or portion thereof at human chromosome 9q34.1 can comprise a genomic region or portion thereof at chr9:132262446-132370055, the genomic region or portion thereof at human chromosome 11p15.4 can comprise a genomic region or portion thereof at chr11:2904813-2907001, 17q21.33 can comprise a genomic region or portion thereof at chr17: 47454237-47654582, the genomic region or portion thereof at human chromosome 17q25.3 can comprise a genomic region or portion thereof at chr17:77702278-77862768, the genomic region or portion thereof at human chromosome 22q13.1 can comprise a genomic region or portion thereof at chr22:39620241-39631867, the genomic region or portion thereof at human chromosome 4p13 can comprise a genomic region or portion thereof at chr4:44558370-44559188, the genomic region or portion thereof at human chromosome 5q13.1 can comprise a genomic region or portion thereof at chr5:67803220-67803609, the genomic region or portion thereof at human chromosome 5q14.3 can comprise a genomic region or portion thereof at chr5:85936281-86082787, the genomic region or portion thereof at human chromosome 5q21.1 can comprise a genomic region or portion thereof at chr5:102652546-102813426, the genomic region or portion thereof at human chromosome 5q21.2 can comprise a genomic region or portion thereof at chr5: 103047961-103230737, the genomic region or portion thereof at human chromosome 5q21.3 can comprise a genomic region or portion thereof at chr5:108476063-108523316, the genomic region or portion thereof at human chromosome 5q23.1 can comprise a genomic region or portion thereof at chr5:116987516-116987850, at the genomic region or portion thereof human chromosome 6q14.1 can comprise a genomic region or portion thereof at chr6:79240539-79417494, the genomic region or portion thereof at human chromosome 6q21 can comprise one or more genomic regions or portions thereof at chr6: 105514625-105687735 and/or chr6:112401839-112550863, the genomic region or portion thereof at human chromosome 8p22 can comprise a genomic region or portion thereof at chr8:15649576-15649945, the genomic region or portion thereof at human chromosome 8p21.2 can comprise one or more genomic regions or portions thereof at chr8:25189716-25280826, chr8:26260492-26362544, and/or chr8: 26555762-26676439, the genomic region or portion thereof at human chromosome 8p12 can comprise a genomic region or portion thereof at chr8:32412399-32572832, the genomic region or portion thereof at human chromosome 10q23.31 can comprise a genomic region or portion thereof at chr10: 89991491-90075908, the genomic region or portion thereof at human chromosome 13q14.11 can comprise one or more genomic regions or portions thereof at chr13:40129477-40205232, chr13:41044273-41044745, and/or chr13: 43679675-43868415, the genomic region or portion thereof at human chromosome 13q14.13 can comprise a genomic region or portion thereof at chr13:45857696-45858096, the genomic region or portion thereof at human chromosome 13q14.2 can comprise a genomic region or portion thereof at chr13:49015662-49140264, the genomic region or portion thereof at human chromosome 13q14.3 can comprise a genomic region or portion thereof at chr13:51245126-51245378 and the genomic region or portion thereof at human chromosome 16q23.1 can comprise a genomic region or portion thereof at chr16:77158148-77311367. Specific genomic regions or portions thereof that are located at human chromosomes 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 and 16q23.1 are provided in Table 1.

In some instances, the set of determined clinical factors comprises the PSA level (e.g., a preoperative PSA level), the pathogenic Gleason score, the surgical margin status, the presence of extracapsular extension, the presence of seminal vesicle, and the presence of lymph node involvement.

In yet another aspect, provided herein is a method of determining a risk of prostate cancer in a human subject. The method includes (a) assigning a value to: (i) a cellular copy number of a nucleic acid encoding a genomic region or portion thereof in a first sample from the subject; (ii) one or more of: interleukin 6 soluble receptor (IL6SR) expression and prostate specific antigen (PSA) expression in a second sample from the subject; and (iii) one or more of: a cellular pattern, a surgical margin, an extracapsular extension, a seminal vesical invasion and a lymph node invasion, in the prostate gland of the subject; (b) assigning a score based on the values; and (c) determining the risk of prostate cancer based on the score.

In some embodiments, the method further includes comparing the copy number of the genomic region or portion thereof in the first sample to a copy number of the genomic region or portion thereof in a non-cancer cell. The first sample can be a sample containing a cancer cell. In some instances, the method also includes hybridizing the genomic region or portion thereof to a nucleic acid comprising a sequence that is at least 50% complementary to the genomic region or portion thereof. In other instances, the method also includes contacting the genomic region or portion thereof with an array of nucleic acids, wherein at least one of the nucleic acids is at least 50% complementary to the genomic region or portion thereof.

In some embodiments, the step of comparing the copy number can include detecting single nucleotide polymorphisms (SNPs). The step of comparing the copy number can also comprise quantifying the number of copies of DNA per cell that encodes the genomic region or portion thereof. In some cases, comparing the copy number includes reverse transcribing RNA that encodes the genomic region or portion thereof into cDNA and quantifying the cDNA produced from RNA.

In some embodiments, the genomic region or portion thereof is selected from one or more of a genomic location selected from the group consisting of 2qtel, 3q26.2, 3q26.32, 5p15.1, 7p22.3, 7q11.23, 7q11.22, 7q22.1, 7q31.31, 9q34.11, 11p15.5, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 8q, 10q23.31, 13q14.11, 13q14.13, 13q14.2, 13q14 and 16q23.1. In other embodiments, the genomic region or portion thereof comprises a gene selected from one or more of EV11, PIK3CA, EIF3S9, ELN, AUTS2, VGF, Serpinel, PLOD3, AP1S1, CORTBP2, p57 (KIP2), NGFR, CBX4, CBX8, PDGFB, FER, TUBE1, LAMA4, BVES, POPDC3, TUSC3, DOCK5, BNIP3L, ADRA1, NRG1, LHFP, GTF2F2, RB1, CHC1L and MYC.

In some embodiments, the method additionally includes detecting a transforming growth factor beta (TGFβ) protein expression level. The method can also include detecting a prostate specific antigen expression level in the second sample. The score can be influenced by the prostate specific antigen expression level.

In some embodiments, IL6SR expression is detected as part of assigning the value. The step of detecting IL6SR expression can include detecting a quantity (amount or level) of IL6SR protein.

In some embodiments, the first sample and the second sample are the same, e.g., the same sample. In some embodiments, the first and second samples are not the same sample, e.g., different samples. For example, the first sample may be a metastatic tissue sample and the second sample may be a blood sample. In some cases, the first and/or second sample is selected from a lymph node sample, a prostate tissue sample, a blood sample, a serum sample, a plasma sample and combinations thereof. The first and second sample can be different samples of the sample type. For instances, the first and second samples can be two different lymph node samples.

In some embodiments, the subject has been diagnosed as having prostate cancer. In other embodiments, the subject has had surgery for removal of cancerous prostate tissue and the determining the risk of prostate cancer provides a risk level for recurrence of prostate cancer. The surgery may have been radical prostatectomy. In yet other embodiments, the subject is diagnosed as having prostate cancer and either a therapeutic intervention, e.g., surgery or disease management, e.g., active surveillance is being selected.

In some embodiments, the risk of prostate cancer comprises the risk of prostate cancer metastasis, the risk of prostate cancer recurrence and/or the risk of a stage of the prostate cancer.

In some embodiments, the score indicates that the subject has an above-average likelihood of reoccurrence and the method further comprises treating the subject to kill, inhibit, or remove prostate cancer cells. In other embodiments, the score indicates that the subject has an average or below-average likelihood of reoccurrence and the method further comprises committing the subject to watchful waiting.

The method can include designating numerical values to a gene copy number(s), expression biomarker(s), such as RNA or protein biomarker(s), and clinical variable(s); transforming the numerical values into a score, and determining the subject's risk of recurrence, progression, and/or metastatic potential of prostate cancer. An increase or decrease in one or more of the gene copy numbers, expression biomarkers and clinical variables as compared to a reference standard may indicate that prostate cancer is prone to recur, progress, and/or metastasize.

In a further aspect, provided herein is a method for evaluating a biopsy sample to determine a likelihood that a prostate tumor will be aggressive, wherein the method comprises: (a) detecting copy numbers for a set of genomic regions or portions thereof in a nucleic acid sample from a biopsy sample obtained from a human patient, e.g., that has not received an initial therapy to treat the prostate tumor; wherein the set of genomic regions or portions thereof comprises genomic regions or portions thereof at human chromosomes 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 or 16q23.1; (b) scoring each genomic region or portion thereof as diseased or normal, wherein the scoring is determined based on the copy number of the biopsy sample compared to a reference copy number; and the genomic region or portion thereof is scored as diseased if there is an increase in copy number at the genomic region or portion thereof located at human chromosome 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, or 22813.1 in the biopsy sample compared to the reference copy number, and if there is a decrease in copy number at the genomic region or portion thereof located at human chromosome 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 or 16q23.1 in the biopsy sample compared to reference copy number; and (c) predicting an increased risk of aggressiveness of the prostate tumor when a threshold value of the genomic regions, or portions thereof, are scored as diseased. In some embodiments, a patient is treated with a therapy to kill, inhibit, or remove prostate cancer cells when the patient is predicted to have an increased risk of aggressiveness of the prostate tumor. In other embodiments, a patient is committed to active surveillance when the patient is not predicted to have a risk of prostate tumor aggressiveness. In some embodiments, a patient is predicted to have an increased risk of aggressiveness when at least 20% of the genomic regions or portions thereof are scored as diseased. In some embodiments, the threshold value for tumor aggressiveness corresponds to at least 10%, e.g., 10%, 11%, 12%, 13%, 14%, 15%, 16%, 17%, 18%, 19%, 20%, or more of the set of genomic regions or portions thereof being scored as diseased. In some cases, the threshold value corresponds to at least 15%, e.g., 15%, 16%, 17%, 18%, 19%, 20%, or more of the set of genomic regions or portions thereof being scored as diseased. In other cases, the threshold value corresponds to at least 20%, e.g., 20%, 21%, 22%, 23%, 24%, 25%, 26%, 27%, 28%, 29%, 30%, 31%, 32%, 33%, 34%, 35%, 36%, 37%, 38%, 39%, 40% or more of the set of genomic regions or portions thereof being scored as diseased. In some embodiments, the biopsy sample is from a prostate tumor that has a Gleason score of ≤3+3 and a clinical stage of ≤T2. In some embodiments, the patient may also have a PSA level of ≤10 ng/ml. In some embodiments, the method further comprises evaluating a clinical factor, such as Gleason score, clinical stage, and/or PSA level, to determine a clinical score.

In some embodiments, the set of genomic regions or portions thereof comprises one or more e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 genomic regions or portions thereof selected from the group consisting of human chromosome(s) 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 and 16q23.1.

In other embodiments, the set of genomic regions or portions comprises the genomic regions or portions thereof at human chromosomes 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 and 16q23.1. The genomic region or portion thereof at human chromosome 3q26.2 can comprise a genomic region or portion thereof at chr3:168805847-168806351, the genomic region or portion thereof at human chromosome 3q26.32 can comprise a genomic region or portion thereof at chr3:177272862-177430308, the genomic region or portion thereof at human chromosome 3q26.3 can comprise a genomic region or portion thereof at chr3:178951957-178952231, the genomic region or portion thereof at human chromosome 5p15.1 can comprise a genomic region or portion thereof at chr5:17412420-17592769, the genomic region or portion thereof at human chromosome 7p22.3 can comprise one or more genomic region(s) or portion(s) thereof at chr7:1062717-1063110 and/or chr7:2396631-2396986, the genomic region or portion thereof at human chromosome 7q11.22 can comprise a genomic region or portion thereof at chr7:69577003-69759243, the genomic region or portion thereof at human chromosome 7q11.23 can comprise a genomic region or portion thereof at chr7:73442517-73483030, the genomic region or portion thereof at human chromosome 7q22.1 can comprise a genomic region or portion thereof at chr7:100705095-100899914, the genomic region or portion thereof at human chromosome 7q31.31 can comprise a genomic region or portion thereof at chr7:117432355-117432817, the genomic region or portion thereof at human chromosome 9q34.1 can comprise a genomic region or portion thereof at chr9:132262446-132370055, the genomic region or portion thereof at human chromosome 11p15.4 can comprise a genomic region or portion thereof at chr11:2904813-2907001, 17q21.33 can comprise a genomic region or portion thereof at chr17:47454237-47654582, the genomic region or portion thereof at human chromosome 17q25.3 can comprise a genomic region or portion thereof at chr17:77702278-77862768, the genomic region or portion thereof at human chromosome 22q13.1 can comprise a genomic region or portion thereof at chr22:39620241-39631867, the genomic region or portion thereof at human chromosome 4p13 can comprise a genomic region or portion thereof at chr4:44558370-44559188, the genomic region or portion thereof at human chromosome 5q13.1 can comprise a genomic region or portion thereof at chr5:67803220-67803609, the genomic region or portion thereof at human chromosome 5q14.3 can comprise a genomic region or portion thereof at chr5:85936281-86082787, the genomic region or portion thereof at human chromosome 5q21.1 can comprise a genomic region or portion thereof at chr5:102652546-102813426, the genomic region or portion thereof at human chromosome 5q21.2 can comprise a genomic region or portion thereof at chr5:103047961-103230737, the genomic region or portion thereof at human chromosome 5q21.3 can comprise a genomic region or portion thereof at chr5:108476063-108523316, the genomic region or portion thereof at human chromosome 5q23.1 can comprise a genomic region or portion thereof at chr5:116987516-116987850, at the genomic region or portion thereof human chromosome 6q14.1 can comprise a genomic region or portion thereof at chr6:79240539-79417494, the genomic region or portion thereof at human chromosome 6q21 can comprise one or more genomic region(s) or portion(s) thereof at chr6:105514625-105687735 and/or chr6:112401839-112550863, the genomic region or portion thereof at human chromosome 8p22 can comprise a genomic region or portion thereof at chr8:15649576-15649945, the genomic region or portion thereof at human chromosome 8p21.2 can comprise one or more genomic region(s) or portion(s) thereof at chr8:25189716-25280826, chr8:26260492-26362544, and/or chr8:26555762-26676439, the genomic region or portion thereof at human chromosome 8p12 can comprise a genomic region or portion thereof at chr8:32412399-32572832, the genomic region or portion thereof at human chromosome 10q23.31 can comprise a genomic region or portion thereof at chr10:89991491-90075908, the genomic region or portion thereof at human chromosome 13q14.11 can comprise one or more genomic region(s) or portion(s) thereof at chr13:40129477-40205232, chr13:41044273-41044745, and/or chr13:43679675-43868415, the genomic region or portion thereof at human chromosome 13q14.13 can comprise a genomic region or portion thereof at chr13:45857696-45858096, the genomic region or portion thereof at human chromosome 13q14.2 can comprise a genomic region or portion thereof at chr13:49015662-49140264, the genomic region or portion thereof at human chromosome 13q14.3 can comprise a genomic region or portion thereof at chr13:51245126-51245378 and the genomic region or portion thereof at human chromosome 16q23.1 can comprise a genomic region or portion thereof at chr16:77158148-77311367. Specific genomic regions or portions thereof that are located at human chromosomes 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 and 16q23.1 are provided in Table 1.

In a further aspect, provided herein is a computer product comprising a non-transitory computer readable medium storing a plurality of instructions that when executed determine from a biopsy of a prostate tumor a human subject's risk of having a prostate tumor that will be aggressive, the instructions comprising:

receiving a set of determined copy numbers for a set of genomic regions, or portions thereof, wherein the set of genomic regions or portions thereof comprises genomic regions or portions thereof at human chromosomes g 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 or 16q23.1; and further, wherein the set of determined copy numbers is from a biopsy sample of a prostate tumor from a human patient, e.g., that has not received an initial therapy to treat the prostate tumor;

comparing the set of determined copy numbers to a set of reference copy numbers for the corresponding set of genomic regions or portions thereof;

scoring each genomic region or portion thereof as diseased or normal, wherein the genomic region or portion thereof is diseased if there is an increase in copy number at the genomic region or portion thereof at human chromosome 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, or 22813.1 in the biopsy sample compared to the reference copy number, and if there is a decrease in copy number at the genomic region or portion thereof at human chromosome 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 or 16q23.1 in the biopsy sample compared to the reference copy number; and comparing the number of genomic regions or portions thereof that are scored as diseased to a threshold value for prostate tumor aggressiveness to generate a copy number score that indicates a likelihood that a prostate tumor will be aggressive. In some embodiments, the threshold value corresponds to at least 20% of the genomic regions or portions thereof being scored as diseased. In some embodiments, the threshold value for tumor aggressiveness corresponds to at least 10%, e.g., 10%, 11%, 12%, 13%, 14%, 15%, 16%, 17%, 18%, 19%, 20%, or more of the set of genomic regions or portions thereof being scored as diseased. In some cases, the threshold value corresponds to at least 15%, e.g., 15%, 16%, 17%, 18%, 19%, 20%, or more of the set of genomic regions or portions thereof being scored as diseased. In other cases, the threshold value corresponds to at least 20%, e.g., 20%, 21%, 22%, 23%, 24%, 25%, 26%, 27%, 28%, 29%, 30%, 31%, 32%, 33%, 34%, 35%, 36%, 37%, 38%, 39%, 40% or more of the set of genomic regions or portions thereof being scored as diseased. In some embodiments, the biopsy sample is from a prostate tumor that has a Gleason score of ≤3+3 and a clinical stage of ≤T2. In some embodiments, the patient may also have a PSA level of ≤10 ng/ml. In some embodiments, the computer product further comprises instructions comprising a clinical score, e.g., generated based on clinical factors such as Gleason score, clinical stage, and/or PSA level.

In some embodiments, the set of genomic regions or portions thereof comprises one or more e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 genomic regions or portions thereof selected from the group consisting of human chromosome(s) 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 and 16q23.1.

In other embodiments, the set of genomic regions or portions comprises the genomic regions or portions thereof at human chromosomes 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 and 16q23.1. The genomic region or portion thereof at human chromosome 3q26.2 can comprise a genomic region or portion thereof at chr3:168805847-168806351, the genomic region or portion thereof at human chromosome 3q26.32 can comprise a genomic region or portion thereof at chr3: 177272862-177430308, the genomic region or portion thereof at human chromosome 3q26.3 can comprise a genomic region or portion thereof at chr3:178951957-178952231, the genomic region or portion thereof at human chromosome 5p15.1 can comprise a genomic region or portion thereof at chr5:17412420-17592769, the genomic region or portion thereof at human chromosome 7p22.3 can comprise one or more genomic region(s) or portion(s) thereof at chr7:1062717-1063110 and/or chr7:2396631-2396986, the genomic region or portion thereof at human chromosome 7q11.22 can comprise a genomic region or portion thereof at chr7:69577003-69759243, the genomic region or portion thereof at human chromosome 7q11.23 can comprise a genomic region or portion thereof at chr7: 73442517-73483030, the genomic region or portion thereof at human chromosome 7q22.1 can comprise a genomic region or portion thereof at chr7:100705095-100899914, the genomic region or portion thereof at human chromosome 7q31.31 can comprise a genomic region or portion thereof at chr7:117432355-117432817, the genomic region or portion thereof at human chromosome 9q34.1 can comprise a genomic region or portion thereof at chr9:132262446-132370055, the genomic region or portion thereof at human chromosome 11p15.4 can comprise a genomic region or portion thereof at chr11:2904813-2907001, 17q21.33 can comprise a genomic region or portion thereof at chr17: 47454237-47654582, the genomic region or portion thereof at human chromosome 17q25.3 can comprise a genomic region or portion thereof at chr17:77702278-77862768, the genomic region or portion thereof at human chromosome 22q13.1 can comprise a genomic region or portion thereof at chr22:39620241-39631867, the genomic region or portion thereof at human chromosome 4p13 can comprise a genomic region or portion thereof at chr4:44558370-44559188, the genomic region or portion thereof at human chromosome 5q13.1 can comprise a genomic region or portion thereof at chr5:67803220-67803609, the genomic region or portion thereof at human chromosome 5q14.3 can comprise a genomic region or portion thereof at chr5:85936281-86082787, the genomic region or portion thereof at human chromosome 5q21.1 can comprise a genomic region or portion thereof at chr5:102652546-102813426, the genomic region or portion thereof at human chromosome 5q21.2 can comprise a genomic region or portion thereof at chr5: 103047961-103230737, the genomic region or portion thereof at human chromosome 5q21.3 can comprise a genomic region or portion thereof at chr5:108476063-108523316, the genomic region or portion thereof at human chromosome 5q23.1 can comprise a genomic region or portion thereof at chr5:116987516-116987850, at the genomic region or portion thereof human chromosome 6q14.1 can comprise a genomic region or portion thereof at chr6:79240539-79417494, the genomic region or portion thereof at human chromosome 6q21 can comprise one or more genomic region(s) or portion(s) thereof at chr6: 105514625-105687735 and/or chr6:112401839-112550863, the genomic region or portion thereof at human chromosome 8p22 can comprise a genomic region or portion thereof at chr8:15649576-15649945, the genomic region or portion thereof at human chromosome 8p21.2 can comprise one or more genomic region(s) or portion(s) thereof at chr8: 25189716-25280826, chr8:26260492-26362544, and/or chr8:26555762-26676439, the genomic region or portion thereof at human chromosome 8p12 can comprise a genomic region or portion thereof at chr8:32412399-32572832, the genomic region or portion thereof at human chromosome 10q23.31 can comprise a genomic region or portion thereof at chr10:89991491-90075908, the genomic region or portion thereof at human chromosome 13q14.11 can comprise one or more genomic region(s) or portion(s) thereof at chr13: 40129477-40205232, chr13:41044273-41044745, and/or chr13:43679675-43868415, the genomic region or portion thereof at human chromosome 13q14.13 can comprise a genomic region or portion thereof at chr13:45857696-45858096, the genomic region or portion thereof at human chromosome 13q14.2 can comprise a genomic region or portion thereof at chr13:49015662-49140264, the genomic region or portion thereof at human chromosome 13q14.3 can comprise a genomic region or portion thereof at chr13: 51245126-51245378 and the genomic region or portion thereof at human chromosome 16q23.1 can comprise a genomic region or portion thereof at chr16:77158148-77311367. Specific genomic regions or portions thereof that are located at human chromosomes 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 and 16q23.1 are provided in Table 1.

In a further aspect, described herein is a computer-implemented method for determining a risk of prostate tumor aggressiveness: (a) receiving, at one or more computer system(s), information about a set of copy numbers for a set of genomic regions or portions thereof wherein the set of genomic regions or portions thereof comprises genomic regions or portions thereof at human chromosomes 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3, or 16q23.1; wherein the copy numbers are determined from a biopsy sample of a prostate tumor from a human patient, e.g., that has not received a initial the ray to treat the prostate tumor; (b) performing, with one or more processors associated with the computer system(s), a comparison of the set of copy numbers in the biopsy sample to a set of reference copy numbers to score the genomic region or portion thereof as diseased or normal, wherein the genomic region or portion thereof is diseased if there is an increase in copy number at the genomic region or portion thereof at human chromosome 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, or 22813.1 in the biopsy sample compared to the reference copy number, and if there is a decrease in copy number at the genomic region or portion thereof at human chromosome 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 or 16q23.1 in the biopsy sample compared to the reference copy number; (c) performing, with one or more processors associated with the computer system(s), a comparison of the number of genomic regions or portions thereof that are scored as diseased to a threshold value for tumor aggressiveness to generate a copy number score; (d) generating, with one or more processors associated with the computer system(s), a determination of a risk of prostate tumor aggressiveness, wherein the risk is higher when the copy number score exceeds the threshold value. In some embodiments, the threshold value corresponds to at least 20% of the genomic regions or portions thereof being scored as diseased. In some embodiments, the threshold value for tumor aggressiveness corresponds to at least 10%, e.g., 10%, 11%, 12%, 13%, 14%, 15%, 16%, 17%, 18%, 19%, 20%, or more of the set of genomic regions or portions thereof being scored as diseased. In some cases, the threshold value corresponds to at least 15%, e.g., 15%, 16%, 17%, 18%, 19%, 20%, or more of the set of genomic regions or portions thereof being scored as diseased. In other cases, the threshold value corresponds to at least 20%, e.g., 20%, 21%, 22%, 23%, 24%, 25%, 26%, 27%, 28%, 29%, 30%, 31%, 32%, 33%, 34%, 35%, 36%, 37%, 38%, 39%, 40% or more of the set of genomic regions or portions thereof being scored as diseased. In some embodiments, the biopsy sample is from a prostate tumor that has a Gleason score of ≤3+3 and a clinical stage of ≤T2. In some embodiments, the patient may also have a PSA level of ≤10 ng/ml. In some embodiments, the further comprises generating a clinical score, e.g., based on clinical factors such as Gleason score, clinical stage, and/or PSA level.

In some embodiments, the set of genomic regions or portions thereof comprises one or more e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32 genomic regions or portions thereof selected from the group consisting of human chromosome(s) 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 and 16q23.1.

In other embodiments, the set of genomic regions or portions comprises the genomic regions or portions thereof at human chromosomes 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 and 16q23.1. The genomic region or portion thereof at human chromosome 3q26.2 can comprise a genomic region or portion thereof at chr3:168805847-168806351, the genomic region or portion thereof at human chromosome 3q26.32 can comprise a genomic region or portion thereof at chr3: 177272862-177430308, the genomic region or portion thereof at human chromosome 3q26.3 can comprise a genomic region or portion thereof at chr3:178951957-178952231, the genomic region or portion thereof at human chromosome 5p15.1 can comprise a genomic region or portion thereof at chr5:17412420-17592769, the genomic region or portion thereof at human chromosome 7p22.3 can comprise one or more genomic region(s) or portion(s) thereof at chr7:1062717-1063110 and/or chr7:2396631-2396986, the genomic region or portion thereof at human chromosome 7q11.22 can comprise a genomic region or portion thereof at chr7:69577003-69759243, the genomic region or portion thereof at human chromosome 7q11.23 can comprise a genomic region or portion thereof at chr7: 73442517-73483030, the genomic region or portion thereof at human chromosome 7q22.1 can comprise a genomic region or portion thereof at chr7:100705095-100899914, the genomic region or portion thereof at human chromosome 7q31.31 can comprise a genomic region or portion thereof at chr7:117432355-117432817, the genomic region or portion thereof at human chromosome 9q34.1 can comprise a genomic region or portion thereof at chr9:132262446-132370055, the genomic region or portion thereof at human chromosome 11p15.4 can comprise a genomic region or portion thereof at chr11:2904813-2907001, 17q21.33 can comprise a genomic region or portion thereof at chr17: 47454237-47654582, the genomic region or portion thereof at human chromosome 17q25.3 can comprise a genomic region or portion thereof at chr17:77702278-77862768, the genomic region or portion thereof at human chromosome 22q13.1 can comprise a genomic region or portion thereof at chr22:39620241-39631867, the genomic region or portion thereof at human chromosome 4p13 can comprise a genomic region or portion thereof at chr4:44558370-44559188, the genomic region or portion thereof at human chromosome 5q13.1 can comprise a genomic region or portion thereof at chr5:67803220-67803609, the genomic region or portion thereof at human chromosome 5q14.3 can comprise a genomic region or portion thereof at chr5:85936281-86082787, the genomic region or portion thereof at human chromosome 5q21.1 can comprise a genomic region or portion thereof at chr5:102652546-102813426, the genomic region or portion thereof at human chromosome 5q21.2 can comprise a genomic region or portion thereof at chr5: 103047961-103230737, the genomic region or portion thereof at human chromosome 5q21.3 can comprise a genomic region or portion thereof at chr5:108476063-108523316, the genomic region or portion thereof at human chromosome 5q23.1 can comprise a genomic region or portion thereof at chr5:116987516-116987850, at the genomic region or portion thereof human chromosome 6q14.1 can comprise a genomic region or portion thereof at chr6:79240539-79417494, the genomic region or portion thereof at human chromosome 6q21 can comprise one or more genomic region(s) or portion(s) thereof at chr6: 105514625-105687735 and/or chr6:112401839-112550863, the genomic region or portion thereof at human chromosome 8p22 can comprise a genomic region or portion thereof at chr8:15649576-15649945, the genomic region or portion thereof at human chromosome 8p21.2 can comprise one or more genomic region(s) or portion(s) thereof at chr8: 25189716-25280826, chr8:26260492-26362544, and/or chr8:26555762-26676439, the genomic region or portion thereof at human chromosome 8p12 can comprise a genomic region or portion thereof at chr8:32412399-32572832, the genomic region or portion thereof at human chromosome 10q23.31 can comprise a genomic region or portion thereof at chr10:89991491-90075908, the genomic region or portion thereof at human chromosome 13q14.11 can comprise one or more genomic region(s) or portion(s) thereof at chr13: 40129477-40205232, chr13:41044273-41044745, and/or chr13:43679675-43868415, the genomic region or portion thereof at human chromosome 13q14.13 can comprise a genomic region or portion thereof at chr13:45857696-45858096, the genomic region or portion thereof at human chromosome 13q14.2 can comprise a genomic region or portion thereof at chr13:49015662-49140264, the genomic region or portion thereof at human chromosome 13q14.3 can comprise a genomic region or portion thereof at chr13: 51245126-51245378 and the genomic region or portion thereof at human chromosome 16q23.1 can comprise a genomic region or portion thereof at chr16:77158148-77311367. Specific genomic regions or portions thereof that are located at human chromosomes 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 and 16q23.1 are provided in Table 1.

In some embodiments, the risk of tumor aggressiveness evaluation may comprise designating numerical values to a gene copy number(s), expression biomarker(s), such as RNA or protein biomarker(s), and clinical variable(s); transforming the numerical values into a score, and determining the subject's risk of having an aggressive tumor.

Other objects, features, and advantages of the present invention will be apparent to one of skill in the art from the following detailed description and figures.

BRIEF DESCRIPTION OF THE DRAWINGS

FIG. 1 shows a block diagram of an example computer system 100 usable with system and methods according to embodiments of the present disclosure.

DETAILED DESCRIPTION OF THE INVENTION

Provided herein are methods and systems for determining the risk of a subject developing or having an aggressive form of prostate cancer, such as rapidly growing prostate cancer or a form of prostate cancer with a likelihood of recurrence and/or metastasis. The method can be used for subjects previously treated for prostate cancer (e.g., having prostate surgery including but not limited to radical prostatectomy) to determine their likelihood of reoccurrence of prostate cancer. The methods involve detection of copy number aberrations, e.g., cellular copy number variants or SNPs at one or more specific genomic regions in a sample obtained from the subject, and one or more clinical variables including PSA level, cellular pattern, surgical margin, extracapsular extension seminal vesical invasion and lymph node invasion in the prostate gland of the subject. The inventors combined the above-listed criteria to develop a method that has high sensitivity and specificity for predicting reoccurrence of prostate cancer.

I. DEFINITIONS

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "prostate cancer" refers to proliferative lesion or abnormality of the prostate. Prostate cancer includes benign lesions, premalignant lesions, malignant lesions, as well as solid tumors and metastatic disease.

The term "risk of prostate cancer," in the context of a subject, refers to a risk of cancer recurrence, progression, or metastasis of prostate cancer in a subject who currently has prostate cancer, a subject who previously has had prostate cancer, or a subject at risk of developing aggressive prostate cancer, e.g., a rapidly growing form of prostate cancer or a form of prostate cancer having a likelihood of recurrence, progression and/or metastasis. A subject at risk of developing aggressive prostate cancer can be genetically predisposed to prostate cancer, e.g., a family history of have a mutation in a gene that causes prostate cancer. Alternatively, a subject at risk of developing aggressive prostate cancer can show early signs or symptoms of prostate cancer, such as hyperplasia. A subject currently with prostate cancer has one or more of the symptoms of the disease and may have been diagnosed with prostate cancer.

The term "cellular copy number" or "copy number" refers to a number of copies of a gene, a genomic region or a portion thereof in the genome of a subject. The terms "copy number variation" and "copy number aberration," which can be used interchangeably, refer to a structural variation or alteration of genomic DNA, e.g., a gene, genomic region, or a portion thereof that results in a cell having an abnormal number of copies of one or more genes.

The terms "determining," "assessing," "assaying," "measuring" and "detecting" can be used interchangeably and refer to both quantitative and semi-quantitative determinations. Where either a quantitative and semi-quantitative determination is intended, the phrase "determining a level" of a biomarker or "detecting" a biomarker is used.

The term "hybridizing" refers to the binding, duplexing, or hybridizing of a nucleic acid molecule preferentially to a particular nucleotide sequence under stringent conditions. The term "stringent conditions" refers to conditions under which a probe will hybridize preferentially to its target subsequence, and to a lesser extent to, or not at all to, other sequences in a mixed population (e.g., a cell lysate or DNA preparation from a tissue biopsy). A "stringent hybridization" and "stringent hybridization wash conditions" in the context of nucleic acid hybridization (e.g., as in array, Southern or northern hybridizations) are sequence dependent, and are different under different environmental parameters. An extensive guide to the hybridization of nucleic acids is found in, e.g., Tijssen (1993) Laboratory Techniques in Biochemistry and Molecular Biology—Hybridization with Nucleic Acid Probes part I, Ch. 2, "Overview of principles of hybridization and the strategy of nucleic acid probe assays," Elsevier, N.Y. Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 50 complementary residues on an array or on a filter in a Southern or northern blot is 42° C. using standard hybridization solutions (see, e.g., Sambrook and Russell (2001) Molecular Cloning: A Laboratory Manual (3rd ed.) Vol. 1-3, Cold Spring Harbor Laboratory, Cold Spring Harbor Press, NY). An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. An example of a low stringency wash for a duplex of, e.g., more than 100 nucleotides, is 4×SSC to 6×SSC at 40° C. for 15 minutes.

The term "complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

The term "nucleic acid" or "polynucleotide" as used herein refers to a deoxyribonucleotide or ribonucleotide in either single- or double-stranded form. The term encompasses nucleic acids containing known analogues of natural nucleotides which have similar or improved binding properties, for the purposes desired, as the reference nucleic acid. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene (methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). PNAs contain non-ionic backbones, such as N-(2-aminoethyl) glycine units. Phosphorothioate linkages are described in WO 97/03211; WO 96/39154; Mata (1997) Toxicol. Appl. Pharmacol. 144:189-197. Other synthetic backbones encompassed by the term include methyl-phosphonate linkages or alternating methylphosphonate and phosphodiester linkages (Strauss-Soukup (1997) Biochemistry 36: 8692-8698), and benzylphosphonate linkages (Samstag (1996) Antisense Nucleic Acid Drug Dev 6: 153-156).

The term "nucleic acid array" as used herein is a plurality of target elements, each target element comprising one or more nucleic acid molecules (probes) immobilized on one or more solid surfaces to which sample nucleic acids can be hybridized. The nucleic acids of a probe can contain sequence(s) from specific genes or clones. Other probes may contain, for instance, reference sequences. The probes of the arrays may be arranged on the solid surface at different densities. The probe densities will depend upon a number of factors, such as the nature of the label, the solid support, and the like. One of skill will recognize that each probe may comprise a mixture of nucleic acids of different lengths and sequences. Thus, for example, a probe may contain more than one copy of a cloned piece of DNA or RNA, and each copy may be broken into fragments of different lengths. The length and complexity of the nucleic acid fixed onto the target element is not critical to the invention. One of skill can adjust these factors to provide optimum hybridization and signal production for a given hybridization procedure, and to provide the required resolution among different genes or genomic locations.

The term "prostatectomy" refers to the removal of prostate tissue by a skilled clinician, such as a surgeon. Non-limiting examples include radical prostatectomy; open (traditional) prostatectomy (involving an incision through the perineum); laparoscopic prostatectomy; and robotic (nerve sparing) prostatectomy.

The term "score" refers to a statistically derived value that can provide physicians and caregivers valuable diagnostic and prognostic insight. In some instances, the score provides a projected risk of disease recurrence or disease progression, a projected rate of disease progression, and/or a projected response to a particular therapy. An individual's score can be compared to a reference score or a reference score scale to determine risk of disease recurrence or to assist in the selection of therapeutic intervention or disease management approaches.

The term "treatment," "treat," or "treating" refer to a method of reducing the effects of a disease or condition (e.g., prostate cancer) or symptom of the disease or condition. Thus, in the disclosed method, treatment can refer to a 10%, 20%, 30%, 40%, 50%, 60%, 70%, 80%, 90%, or 100% reduction in the severity of an established disease or condition or symptom of the disease or condition. For example, a method of treating a disease is considered to be a treatment if there is a 10% reduction in one or more symptoms of the disease in a subject as compared to a control. Thus, the reduction can be a 10%, 20%, 30%, 40%, 50%, 60%, 70%, 80%, 90%, 100% or any percent reduction between 10 and 100% as compared to native or control levels. It is understood that treatment does not necessarily refer to a cure or complete ablation of the disease, condition, or symptoms of the disease or condition.

The term "sample" includes a biological sample or a samples from a biological source. Biological samples include samples from body fluids, e.g., blood, plasma, serum, lymph, or urine, or samples derived, e.g., by biopsy, from cells, tissues or organs, preferably prostate tissue suspected to include or essentially consist of prostate carcinoma cells. This also encompasses samples comprising subcellular compartments or organelles, such as the mitochondria, Golgi network or peroxisomes. Techniques for obtaining the aforementioned different types of biological samples are well known in the art. For example, blood samples may be obtained by blood taking while tissue or organ samples are to be obtained, e.g., by biopsy.

The term "recommending" or "suggesting," in the context of a treatment of a disease, refers to making a suggestion or a recommendation for therapeutic intervention (e.g., drug therapy, adjunctive therapy, etc.) and/or disease management which are specifically applicable to the patient.

The term "watchful waiting" or "active surveillance" refers to a therapeutic approach based on closely monitoring for a sign of cancer progression or any change. In some instances, active surveillance includes performing the methods disclosed herein on a regular or periodic basis. If no signs of progressing prostate carcinoma are apparent, further therapeutic measures such as surgery or radiation and their side effects can be delayed and/or avoided (Dall'Era and Carroll, *Curr Opin Urol*, 2009, 19(3):258-62).

II. DETAILED DESCRIPTIONS OF EMBODIMENTS

Described herein are methods for predicting the risk (e.g., the likelihood) of prostate cancer recurrence, prostate cancer progression, and/or metastatic potential of prostate cancer in a subject (e.g., a human subject). In some embodiments, disease recurrence can refer to having two or more consecutive PSA values that are higher than a pre-determined value (e.g., about 0.2 ng/ml) after a primary treatment (e.g., radical prostatectomy). In other embodiments, disease recurrence can refer to a need for administration of a secondary treatment (e.g., adjuvant therapy) within a pre-determined lapse of time (e.g., within 6 months) after a primary treatment (e.g., radical prostatectomy).

The subject of the methods has been diagnosed with prostate cancer and has received primary (initial) treatment for the disease. In some embodiments, the primary treatment includes, but is not limited to, surgery, radiation therapy (radiotherapy), chemotherapy, immunotherapy (including antibody-based therapy), anti-cancer drug therapy, hormone therapy, brachytherapy, steroid therapy, cryotherapy, transurethral resection of the prostate, high intensity focused ultrasound (HIFU), and any combination thereof. Surgery can be performed to remove prostate cancer tissue. In some cases, surgery is radical prostatectomy. In some embodiments, the subject has undergone a treatment regimen that includes radical prostatectomy and has a risk, such as a low risk, intermediate risk, or high risk of cancer relapse or recurrence. The methods described herein can be used to determine or predict whether the subject has a low risk (a low likelihood or probability), an intermediate risk (an intermediate likelihood or probability), or a high risk (a high likelihood or probability) of cancer relapse or recurrence.

The present disclosure additionally describes methods of predicting whether a primary prostate tumor has an increased likelihood of being aggressive, where the methods comprise evaluating the copy number of a set of genomic regions, or portions thereof, in a nucleic acid sample from a biopsy obtained from a primary prostate tumor. In some embodiments, the patient that has not received an initial treatment for the disease. A change in copy number in genomic regions, or portions thereof, in a direction associated with disease that exceeds a threshold value as described herein is indicative of an increased likelihood of aggressiveness of a primary tumor. In some embodiments, the primary tumor has a Gleeson score of 3+3. In some embodiments, the clinical stage of the tumor is ≤T2. In still other embodiments, the patient has a PSA level that is ≤10 ng/ml. In some embodiments, watchful waiting may be recommended for a patient that does not have a pattern of copy number changes in the set of regions that is associated with an aggressive prostate tumor, whereas in other embodiments, a patient that has a pattern of copy number changes in a set of regions that is associate with an aggressive tumor may have surgery and/or an alternative therapy to treat the tumor.

A. Gene Copy Numbers

Determining a risk of prostate cancer recurrence can include detecting or identifying a copy number variation (a cellular copy number variation) at one or more genomic regions (e.g., loci) or portions thereof in a biological sample (e.g., a tumor sample) obtained from the subject compared to a reference copy number for the same genomic region(s). A copy number variation (e.g., copy number aberration) can be a gain in copy number or a loss in copy number relative to a reference copy number for a specific genomic region. The reference copy number can be the copy number at the genomic region found in a normal cell obtained from a healthy subject (e.g., a subject who does not have cancer such as prostate cancer) or a normal (non-cancer cell) obtained from a subject with cancer (e.g., prostate cancer).

The presence of one or more copy number variation(s) at one or more specific genomic region(s) can indicate disease recurrence. In some embodiments, the subject has a copy number variation at one or more genomic regions or portions thereof, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more genomic regions or portions thereof.

The copy number variations (e.g., copy number aberrations) can be located at one or more genomic regions, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or more genomic regions located at human chromosome(s) 3q26.2, 3q26.32, 3q26.3, 5p15.1, 7p22.3, 7q11.22, 7q11.23, 7822.1, 7831.31, 9834.1, 11p15.4, 17q21.33, 17825.3, 22813.1, 4p13, 5813.1, 5814.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 and 16q23.1, or equivalents thereof.

Table 1 provides exemplary genomic region(s) or portion (s) thereof for human chromosomal locations 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 and 16q23.1. The genomic regions disclosed herein refer to base-pair boundaries defined using the University of California Santa Cruz Human Genome Build 19 (hg19). These genomic regions or loci include those known as Genomic Evaluators of Metastatic Prostate Cancer (GEMCaP) biomarkers which are disclosed in Paris et al., Human Molecular Genetics, 13(13): 1303-1313, 2004; Levin et al., *Cancer Epidemiol Biomarkers Prev*, 23(8), 1677-1682, 2014, the contents are hereby incorporated by reference in their entirety for all purposes.

TABLE 1

Gene Loci Indicative of Prostate Cancer Recurrence

| Locus | Location on Human Chromosome | Genomic Location on hg19 | Copy Number Variant or Aberration (Recurrence) |
|---|---|---|---|
| 1 | 3q26.2 | chr3: 168805847-168806351 | Gain |
| 2 | 3q26.32 | chr3: 177272862-177430308 | Gain |
| 3 | 3q26.3 | chr3: 178951957-178952231 | Gain |
| 4 | 5p15.1 | chr5: 17412420-17592769 | Gain |
| 5 | 7p22.3 | chr7: 1062717-1063110 | Gain |
| 6 | 7p22.3 | chr7: 2396631-2396986 | Gain |
| 7 | 7q11.22 | chr7: 69577003-69759243 | Gain |
| 8 | 7q11.23 | chr7: 73442517-73483030 | Gain |
| 9 | 7q22.1 | chr7: 100705095-100899914 | Gain |
| 10 | 7q31.31 | chr7: 117432355-117432817 | Gain |
| 11 | 9q34.1 | chr9: 132262446-13237005 | Gain |
| 12 | 11p15.4 | chr11: 2904813-2907001 | Gain |
| 13 | 17q21.33 | chr17: 47454237-47654582 | Gain |
| 14 | 17q25.3 | chr17: 77702278-77862768 | Gain |
| 15 | 22q13.1 | chr22: 39620241-39631867 | Gain |
| 16 | 4p13 | chr4: 44558370-44559188 | Loss |
| 17 | 5q13.1 | chr5: 67803220-67803609 | Loss |
| 18 | 5q14.3 | chr5: 85936281-86082787 | Loss |
| 19 | 5q21.1 | chr5: 102652546-10281342 | Loss |
| 20 | 5q21.2 | chr5: 103047961-103230737 | Loss |
| 21 | 5q21.3 | chr5: 108476063-108523316 | Loss |
| 22 | 5q23.1 | chr5: 116987516-116987850 | Loss |
| 23 | 6q14.1 | chr6: 79240539-79417494 | Loss |
| 24 | 6q21 | chr6: 105514625-105687735 | Loss |
| 25 | 6q21 | chr6: 112401839-112550863 | Loss |
| 26 | 8p22 | chr8: 15649576-15649945 | Loss |
| 27 | 8p21.2 | chr8: 25189716-25280826 | Loss |
| 28 | 8p21.2 | chr8: 26260492-26262544 | Loss |
| 29 | 8p21.2 | chr8: 26555762-26676439 | Loss |
| 30 | 8p12 | chr8: 32412399-32572832 | Loss |
| 31 | 10q23.31 | chr10: 89991491-90075908 | Loss |
| 32 | 13q14.11 | chr13: 40129477-40205232 | Loss |
| 33 | 13q14.11 | chr13: 41044273-41044745 | Loss |
| 34 | 13q14.11 | chr13: 43679675-43868415 | Loss |
| 35 | 13q14.13 | chr13: 45857696-45858096 | Loss |
| 36 | 13q14.2 | chr13: 49015662-49140264 | Loss |
| 37 | 13q14.3 | chr13: 51245126-51245378 | Loss |
| 38 | 16q23.1 | chr16: 77158148-77311367 | Loss |

"hg19" refers to University of California, Santa Cruz human genome build 19.

A genome region containing a copy number variation can be classified as diseased or normal. If the copy number variation at human chromosome 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, or 22q13.1 is an increase or gain in copy number, then the specific genome region is classified as being diseased. For instance, if a tumor sample from the subject has a higher copy number than a normal sample at human chromosome 3q26.2, such as at chr3: 168805847-168806351, then this genomic region (locus) is classified as diseased in the subject. Each diseased locus can be assigned a numerical value (e.g., "1") which can be used to calculate a copy number score for the subject.

If the copy number variation at human chromosome 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 or 16q23.1 is a decrease in copy number, then the specific genome region is classified as being diseased. Each diseased locus can be assigned a numerical value (e.g., "1") which can be used to calculate a copy number score for the subject. For instance, if a tumor sample from the subject has a lower copy number than a normal sample at human chromosome 13q14.11, such as at chr13: 40129477-40205232, chr13:41044273-41044745, and/or chr13:43679675-43868415, then this genomic region (locus) is classified as diseased in the subject.

A genomic region or portion thereof that is classified as diseased can be given a numerical score (e.g., "1"). If the genomic region or portion thereof is classified as normal or non-disease, a null score (e.g., "0") can be assigned.

A copy number score can be calculated or determined by comparing the number of diseased genomic region to a threshold value. In some cases, if at least 10%, e.g., 10%, 11%, 12%, 13%, 14%, 15%, 16%, 17%, 18%, 19%, 20%, or more of the genomic regions at human chromosome(s) 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 and 16q23.1 are considered diseased, then the copy number score is defined as positive or indicative of a risk of disease recurrence. In other cases, if at least 15%, e.g., 15%, 16%, 17%, 18%, 19%, 20%, 21%, 22%, 23%, 24%, 25%, 26%, 27%, 28%, 29%, 30%, or more of these genomic regions are considered diseased, then the copy number score is defined as positive or indicative of a risk of disease recurrence. In other cases, if at least 20%, e.g., 20%, 21%, 22%, 23%, 24%, 25%, 26%, 27%, 28%, 29%, 30%, or more of these genomic regions are considered diseased, then the copy number score is defined as positive or indicative of a risk of disease recurrence.

In some cases, the copy number score can be established by summing the number of diseased genomic region values. If, for example, 8 out of 38 assayed genomic regions are classified as diseased, then the copy number score of 8 can be assigned. This copy number score can indicate a high risk of prostate cancer recurrence.

In some embodiments, an increase (e.g. a gain) in copy number at 15 loci as set forth in Table 1 and located at human chromosome 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3 and 22q13.1 (compared to a non-cancer cell), and a decrease (e.g., a loss) in copy number at 23 loci as set forth in Table 1 and located at human chromosome 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 and/or 16q23.1 (compared to a non-cancer cell) corresponds to a copy number score indicative of a high risk of disease recurrence or 100% positive loci or 100% genetic biomarker positivity.

Further description of the genomic regions and the copy number score described herein (e.g., a GEMCaP score) can be found, e.g., in Paris et al., Human Molecular Genetics, 13(13):1303-1313, 2004; and Levin et al., *Cancer Epidemiol Biomarkers Prev,* 23(8), 1677-1682, 2014, the contents are hereby incorporated by reference in their entirety for all purposes.

In some embodiments, the method disclosed herein includes detecting or measuring the copy number of one or more loci at one or more genomic locations set forth in Table 1, such as those at human chromosomes 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 8q, 10q23.31, 13q14.11, 13q14.13, 13q14.2, 13q14.3 and 16q23.1, and optionally, 2qtel. In other embodiments, the method includes determining the copy number of one or more genes including, but not limited to, EVI1, PIK3CA, EIF3S9, ELN, AUTS2, VGF, Serpinel, PLOD3, AP1S1, CORTBP2, p57 (KIP2), NGFR, CBX4, CBX8, PDGFB, FER, TUBE1, LAMA4, BVES, POPDC3, TUSC3, DOCKS, BNIP3L, ADRA1, NRG1, LHFP, GTF2F2, RB1, CHC1L and MYC. In some cases, an increase in the copy number (number of copies of DNA per cell) of one or more genomic regions selected from the group consisting of those in Table 1 and located at human chromosome 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3 and/or 22q13.1 compared to the copy number at the corresponding genomic location(s) in a non-cancer cell, indicates an increased risk of prostate cancer recurrence, progression and/or metastasis of prostate cancer.

In some instances, a decrease in the copy number (number of copies per cell of DNA) at one or more genomic regions selected from the group consisting of those in Table 1 and located at human chromosome 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 and/or 16q23.1, compared to the copy number at the corresponding genomic region(s) in a non-cancer cell, indicates an increased risk of prostate cancer recurrence, progression and/or metastasis of prostate cancer. In some cases, one or more loci are found at the human chromosome 7p22.3, 6q21, 8p21.2, and/or 13q14.11.

The copy number of a genomic region can be detected by numerous methods, including but not limited to, using single or low-copy number probes that detect DNA in specific genomic locations, fluorescence in-situ hybridization (FISH), comparative genomic hybridization, nucleic acid arrays, e.g., SNP arrays, DNA arrays, RNA arrays, and oligonucleotide arrays, direct sequencing or pyrosequencing, massively parallel sequencing, high-throughput sequencing, next generation sequencing, and the like. Additionally, nucleic acid amplification techniques can be used, such as polymerase chain reaction (PCR), reverse transcription polymerase chain reaction (RT-PCR), ligase chain reaction (LCR), strand displacement amplification (SDA), and nucleic acid sequence based amplification (NASBA). The copy number can be determined using the method described in, e.g., U.S. Pat. No. 7,482,123.

A copy number variation (e.g., copy number aberration) can be detected in a biological sample taken from a subject. The biological sample can be a prostate cancer tissue sample, a circulating tumor cell sample, a metastatic tissue sample, a lymph node sample, a prostate tissue sample, a blood sample, a serum sample, a plasma sample, and any combination thereof. A prostate tissue sample refers to a sample of prostate tissue isolated from an individual, such as one afflicted with prostate cancer. The sample may be from material removed via a prostatectomy, such as a radical prostatectomy. Alternatively, the prostate tissue sample is obtained by other means, such as needle (core) biopsy or other biopsy techniques, like laterally directed biopsies, the conventional sextant biopsy approach, different combinations of sextant and lateral biopsies, transrectal ultrasound guided prostate biopsy, microdissection, laser capture microdissection, laser microdissection, and others as known to the skilled person.

In some embodiments, determining the copy number variation in a sample includes detecting a single nucleotide polymorphism (SNP) in one or more of the genomic regions or portions thereof described herein. In some cases, a SNP is detected in one or more of the genomic regions set forth in Table 1, and optionally at the telomeric region located at human chromosome 2qtel. In other cases, a SNP is detected in one or more of the following genes: EV11, PIK3CA, EIF3S9, ELN, AUTS2, VGF, Serpinel, PLOD3, AP1S1, CORTBP2, p57 (KIP2), NGFR, CBX4, CBX8, PDGFB, FER, TUBE1, LAMA4, BVES, POPDC3, TUSC3, DOCKS, BNIP3L, ADRA1, NRG1, LHFP, GTF2F2, RB1, CHC1L and MYC.

Any of various methods known in the art can be used to detect SNPs. Useful techniques include, without limitation, polymerase chain reaction (PCR) based analysis, sequence analysis, array analysis, and electrophoretic analysis, which can be used alone or in combination. Material containing nucleic acid for detecting copy number variation and/or SNPs is routinely obtained from individuals. Such material is any biological matter from which nucleic acid can be prepared.

B. Biological Biomarkers

The methods disclosed herein also include determining the presence, absence or level of biological biomarkers, such as interleukin-6 soluble receptor (IL6SR), prostate-specific antigen (PSA), and/or transforming growth factor, beta 1 (TGFβ1 or TGFβ). These biomarkers can be detected in various samples, including but not limited to, prostate cancer tissue samples, circulating tumor cell samples, metastatic tissue samples, lymph node samples, prostate tissue samples, blood samples, serum samples, plasma samples, and any combination thereof. The sample can be a preoperative sample such as a sample obtained from the subject prior to surgery. Baseline levels of PSA, IL6SR, or TGFβ can be measured or detected in a preoperative sample. Alternatively, the sample can be a postoperative sample such as a sample obtained from the subject after surgery.

Interleukin-6 soluble receptor is a 50-55 kDa ligand binding protein that is derived from the extracellular domain of the gp80 receptor (IL-6 receptor subunit alpha or IL-6Rα) and plays a role in inflammation. IL6SR can bind to IL-6 and induce cellular responses by associating with gp130 (see, e.g., Jones et al., *FASEB J*, 2001, 15:43-58). IL6SR can also act as an agonist of IL-6. IL6SR is a member of the type 1 cytokine receptor family, type 3 subfamily.

The human IL-6Rα polypeptide sequence is set forth in, e.g., UniProt No. P08887 or Genbank Accession No. NP_000556. The extracellular domain of IL-6Rα is located from amino acid position 20 to position of 365 of the sequence set forth in UniProt No. P08887. The human IL-6Rα mRNA (coding) sequence is set forth in, e.g., Genbank Accession No. NM_000565.

Prostate-specific antigen is a protein produced by cells of the prostate gland. It is a member of the peptidase S1 family of proteins. The human PSA polypeptide sequence is set forth in, e.g., Genbank Accession Nos. NP_001639, NP_001025218, and NP_001025219. One skilled in the art will appreciate that the human PSA polypeptide has about 5 or more isoforms. The human PSA mRNA (coding) sequence is set forth in, e.g., Genbank Accession Nos. NM_001648, NM_001030047, and NM_001030048.

Transforming growth factor, beta 1 is a secreted protein that plays a role in growth, proliferation, differentiation, apoptosis, and other cellular functions in numerous cell types. It is a member of the transforming growth factor beta superfamily of cytokines. The human TGFβ polypeptide sequence is set forth in, e.g., Genbank Accession No. NP_000651. The human TGFβ mRNA (coding) sequence is set forth in, e.g., Genbank Accession No. NM_000660.

In some embodiments, the mRNA expression of IL6SR, PSA and/or TGFβ is detected in a sample from the subject. The presence, absence or mRNA level of IL6SR6; PSA; TGFβ; IL6SR6 and PSA; IL6SR6 and TGFβ; PSA and TGFβ; or IL6SR, PSA and TGFβ can be measured in a sample.

The presence and/or level of mRNA can be detected by a variety of methods including, but not limited to, reverse-transcription polymerase chain reaction (RT-PCR); quantitative real-time PCR (qRT-PCR); quantitative PCR (TaqMan®); Northern blotting, in situ hybridization, microarray analysis; cDNA-mediated annealing, selection, extension, and ligation; direct sequencing or pyrosequencing; massively parallel sequencing; next generation sequencing; high performance liquid chromatography (HPLC) fragment analysis; capillarity electrophoresis; and the like.

In some embodiments, the protein expression of IL6SR and/or PSA is detected in a sample from the subject. The presence, absence or protein level of IL6SR6; PSA; TGFβ; IL6SR6 and PSA; IL6SR6 and TGFβ; PSA and TGFβ; or IL6SR, PSA and TGFβ can be measured in a sample.

The presence, absence and/or level of protein can be detected by a variety of methods including, but not limited to, Western blotting, immunoassays, e.g., enzyme-linked immunosorbent assay (ELISA), enzyme immunoassay (EIA), radioimmunoassay (RIA), and immunohistochemistry, mass spectrometry, protein array, antibody array, and the like.

Biological biomarker standards (reference values or control values) can be predetermined, determined concurrently, or determined after a sample is obtained from the subject. Biomarker standards for use with the methods described herein can, for example, include data from samples from subjects without prostate cancer, data from samples from subjects with prostate cancer that is not a progressive, recurrent, and/or metastatic prostate cancer, and data from samples from subjects with prostate cancer that is a progressive, recurrent, and/or metastatic prostate cancer. Comparisons can be made to multiple biomarker standards. The standards can be run in the same assay or can be known standards from a previous assay.

C. Risk Assessment Systems

The methods provided herein include assessing risk of prostate cancer recurrence, providing a disease recurrence classification, and/or assessing risk of aggressiveness of a prostate cancer, e.g., before administration of a therapy to treat the prostate cancer. In some embodiments, a postoperative risk assessment (postsurgical risk assessment) can be performed. In some embodiments, the postoperative risk assessment can include the one or more of the following clinical factors (clinical variables or predictors): a PSA level or PSA score (e.g., a preoperative PSA level or PSA score); a pathologic Gleason score (pGS), surgical margin (SM) status, presence or absence of extracapsular extension (ECE), presence or absence of seminal vesicle invasion (SVI), and lymph node involvement (LNI). In other embodiments, the postoperative risk assessment includes 1, 2, 3, 4, 5, or 6 of these clinical factors. For instance, the postoperative risk assessment includes a PSA level or PSA score; a pathologic Gleason score (pGS), surgical margin (SM) status, presence or absence of extracapsular extension (ECE), presence or absence of seminal vesicle invasion (SVI), and lymph node involvement (LNI). The postoperative risk assessment can be the Cancer of the Prostate Risk Assessment Postsurgical (CAPRA-S) score (Cooperberg et al., Cancer, 117:5039-46, 2011) or an equivalent thereof.

A preoperative level of PSA (e.g., a baseline level of PSA) can be measured in a sample obtained from the subject having a possible risk of prostate cancer recurrence. In some embodiments, the level of PSA is compared to a cut-off level. Cut-off levels can be used to classify or categorize the subject, for example, the cut-off ranges can be: (1) equal to or less than 6 ng/ml PSA; (2) 6.01-10 ng/ml PSA; (3) 10.01-20 ng/ml PSA; and (4) greater than 20 ng/ml PSA. The determined PSA level can be converted into a PSA score. In some embodiments, a PSA level of 0-6 ng/ml is assigned a numerical value/score of 0; a PSA level of 6.01-10 ng/ml is assigned a numerical value/score of 1; a PSA level of 10.01-20 ng/ml is assigned a numerical value/score of 2; and a PSA level of greater than 20 ng/ml is assigned a numerical value/score of 3.

In some embodiment, the cellular pattern or microscopic appearance of a prostate sample from a patient is evaluated and compared to a normal, healthy prostate sample. If the test sample appears similar or substantially similar to the healthy sample, the value assigned to the cellular pattern in a low value, e.g., low numerical value. If the test sample appears different than the healthy sample, the value assigned to the cellular pattern in a high value, e.g., high numerical value.

The cellular pattern can be scored according to a standardized scale such as the Gleason score. The term "Gleason score" or "pathologic Gleason score" refers to the grading of a sample of prostate cancer by a trained pathologist according to the Gleason system, which assigns a Gleason score using numbers from 1 to 5 based upon similarities in the cells of a sample of prostate tissue compared to normal prostate tissue. Tissue that looks much like normal prostate tissue is given a score or grade of 1 while a tissue that lacks normal features and the cells seem to be spread haphazardly through the prostate is given a score or grade of 5. Scores, or grades of 2 through 4, inclusive, have features in between these possibilities. The Gleason score is described in, e.g., Gleason, D. F. (1977) Urologic Pathology: The Prostate. Philadelphia: Lea and Febiger. pp. 171-198.

In some embodiments, the pathologic Gleason Score or pGS can be coded via 3 binary indicators that contrast low risk, medium risk, and high risk levels against very low risk levels with pre-determined cut-off values. For instance, a pGS of 2-6 can be assigned a numerical value of 0 points; a pGS of 3+4 can be assigned a numerical value of 1; a pGS of 4+3 can be assigned a numerical value of 2; and a pGS of 8-10 can be assigned a numerical value of 3. An assay that evaluates the pathology of the prostate tumor can be used determine a pGS.

In some embodiments, the method includes determining the presence or absence of a positive surgical margin after surgery. A positive surgical margin (+SM) refers to the presence of tumor extending to the margin of the prostate and is determined by a pathologist. A positive surgical margin is a prognostic indicator of poor outcome. It can indicate an increased risk of local recurrence of prostate cancer. In some instances, a negative SM value can be given a numerical value of 0 in the risk assessment system, and a positive SM value can be given a numerical value of 2. An assay such as a pathological analysis can be performed to detect the presence or absence of a surgical margin (the presence or absence of tumor tissue extending to the margin of the prostate) after surgery.

In some embodiments, the method includes assessing extracapsular extension (ECE) of the prostate gland. Extracapsular extension refers to the presence of tumor cells growing in the tissue surrounding the prostate. The patient can have extracapsular extension with either negative or positive surgical margins. The absence of ECE can be given a value of 0 in the risk assessment system and the presence of ECE can be given a value of 1. An assay such as a pathological analysis can be performed to detect the presence or absence of extracapsular extension after surgery.

In some embodiments, the method includes analyzing the presence of seminal vesicle invasion (SVI) by cancer cells of the prostate gland. If tumor cells are detected in the seminal vesicles, this can indicate an increased risk of tumor recurrence. The absence of SVI can be assigned a value of 0 and the presence of SVI can be assigned a value of 2 in the risk assessment system. An assay such as a pathological analysis can be performed to detect the presence or absence of SVI after surgery.

In some embodiments, the method includes evaluating the appearance of a lymph node invasion (LNI) by cancer cells of the prostate gland. A pathologist can identify cancer cells present or growing into blood vessels or lymphatic channels. The presence of lymph node invasion can indicate an increased risk of cancer recurrence at a site distant from the prostate gland. The absence of LNI can be represented as a value of 0 in the risk assessment system and the presence of LNI can be represented as a value of 1. An assay such as a pathological analysis can be performed to detect the presence or absence of LNI after surgery.

The PSA value, pathologic Gleason score (pGS) value, surgical margin (SM) value, extracapsular extension (ECE) value, seminal vesicle invasion (SVI) value, lymph node involvement (LNI) value, and any combination thereof can be incorporated into a clinical score that can be used to determine prostate cancer recurrence risk. For example, the clinical score can include the PSA value and the pGS value, the PSA value and the SM value, the PSA value and the ECE value, the PSA value and the SVI value, the PSA value and the LNI value, the pGS value and the SM value, the pGS value and the ECE value, the pGS value and the SVI value, the pGS value and the LNI value, the SM value and the ECE value, the SM value and the SVI value, the SM value and the LNI value, the ECE value and the SVI value, the ECE value and the LNI value, the SVI value and the LNI value, the PSA value and the pGS value and the SM value, the PSA value and the pGS value and the ECE value, the PSA value and the pGS value and the SVI value, the PSA value and the pGS value and the LNI value, the PSA value and the SM value and the ECE value, the PSA value and the SM value and the SVI value, the PSA value and the SM value and the LNI value, the PSA value and the ECE value and the SVI value, the PSA value and the ECE value and the LNI value, the PSA value and the SVI value and the LNI value, the pGS value and the ECE value and the SVI value, the pGS value and the ECE value and the LNI value, the pGS value and the SVI value and the LNI value, the ECE value and the SVI value and the LNI value, the PSA value and the pGS value and the SM value and ECE value, the PSA value and the pGS value and the SM value and the SVI value, the PSA value and the pGS value and the SM value and the LNI value, the PSA value and the SM value and the ECE value and the SVI value, the PSA value and the SM value and the ECE value and the LNI value, the PSA value and the ECE value and the SVI value, the pGS value and the SM value and ECE value and SVI value, the pGS value and the SM value and the ECE value and the LNI value, the SM value and the ECE value and the SVI value and the LNI value, the PSA value and the pGS value and the SM value and the ECE value and the SVI value, the PSA value and the pGS value and the SM value and the ECE value and the LNI value, the PSA value and the SM value and the ECE value and the SVI value and the LNI value, the PSA value and the pGS value and the ECE value and the SVI value and the LNI value, the PSA value and the pGS value and the ECE value and the SVI value and the LNI value, the PSA value and the pGS value and the SM value and the SVI value and the LNI value, the PSA value and the pGS value and the SM value and the ECE value and the SVI value and the LNI value, and the like.

For instance, these values can be summed together such that each individual value possesses equal weight. In other embodiments, each individual value can be adjusted such that the values do not have equal weight. Each value can have a different weight in the recurrence risk score. Alternatively, at least two values have a different weight in the disease recurrence risk score.

The range of the clinical score can be set such that a 2-point or more increase in the score equates to at least a doubling of risk of disease recurrence. Alternatively, a 2-point or less increase in the clinical score indicates at least a doubling of risk recurrence.

The calculated clinical score can be expressed as an numerical value, e.g., an integer. In some embodiments, the recurrence score is on a scale that ranges, for instance, from 1 to 9 of higher. A low score on such a scale, e.g., a score of 0-2 on a scale ranging from 0-9 or higher can represent a low risk of disease recurrence. An intermediate score, e.g., a score of 3-5 on a scale ranging from 0-9 or higher can indicate an intermediate risk of disease recurrence. A high score, e.g., a score of 6-10 ranging from 0-9 or higher can indicate a high risk of prostate cancer recurrence. The clinical score can be used as a risk stratification tool or method in a clinical setting.

A calculated prostate cancer recurrence score can also indicate or predict mortality caused by prostate cancer. As such, a low risk of disease recurrence can indicate the subject has a low risk of prostate cancer mortality. Similarly, an intermediate risk of disease recurrence can predict an intermediate risk of prostate cancer mortality, and a high risk of disease recurrence can predict a high risk of prostate cancer mortality.

In some embodiment, a calculated clinical score can be used for selecting therapy for a subject who has undergone primary treatment for prostate cancer. The primary treatment can be radical prostatectomy. Alternatively, the primary treatment can be radiation therapy.

In some cases, the method described herein also include a preoperative risk assessment. Useful preoperative risk assessment approaches include, but are not limited to, the D'Amico risk classification (D'Amico et al., *JAMA*, 1998, 208:969-974), nonograms, such as the Kattan nomogram, and the Cancer of the Prostate Risk Assessment (CAPRA) system (Cooperberg et al., *Cancer*, 2011, 117(22):5039-5046). The CAPRA score is calculated using points corresponding to: the patient's age (0 points for under 50 years old and 1 point for 50 and older), the level of PSA in ng/ml at diagnosis (0 points for PSA<=6, 1 point for between 6.1 to 10, 2 points for between 10.1 and 20, 3 points for between 20.1 and 30, and 4 points for >30), a Gleason score of the biopsy (0 points for no pattern of 4 or 5, 1 point for secondary pattern of 4 or 5, and 3 points for primary pattern of 4 or 5), a clinical T-stage (0 points for T1 or T2, 1 point for T3a), and a percent of biopsy cores positive for cancer (0 points for less than 34%, 1 point for >=34%). The scoring is on a 0 to 10 point scale. A CAPRA score of 0 to 2 indicates a low risk of disease recurrence; a score of 3 to 5 indicates an intermediate risk; and a score of 6 to 10 indicates a high risk.

Clinical staging of prostate cancer can assist a clinician to determine the disease progression or prognosis. In addition, it can help a clinician select treatment options and/or a disease management plan for the patient. Staging may be performed clinically by physical examination, blood tests, or response to radiation therapy, and/or pathologically based on surgery, such as radical prostatectomy. According to the tumor, node, metastasis (TNM) staging system of the American Joint Committee on Cancer (AJCC), AJCC Cancer Staging Manual (7th Ed., 2010), the various stages of prostate cancer are defined as follows: the extent of the primary tumor (Tumor or T category); whether the cancer has spread to nearby lymph nodes (Node or N category); the presence or absence of metastasis (metastasis or M category); PSA level at diagnosis; and Gleason score based on biopsy. The TNM clinical categories are as follows: Tumor: T1: clinically inapparent tumor not palpable or visible by imaging, T1a: tumor incidental histological finding in 5% or less of tissue resected, T1b: tumor incidental histological finding in more than 5% of tissue resected, T1c: tumor identified by needle biopsy; T2: tumor confined within prostate, T2a: tumor involves one half of one lobe or less, T2b: tumor involves more than half of one lobe, but not both lobes, T2c: tumor involves both lobes; T3: tumor extends through the prostatic capsule, T3a: extracapsular extension (unilateral or bilateral), T3b: tumor invades seminal vesicle (s); T4: tumor is fixed or invades adjacent structures other than seminal vesicles (bladder neck, external sphincter, rectum, levator muscles, or pelvic wall). Generally, a clinical T (cT) stage is T1 or T2 and pathologic T (pT) stage is T2 or higher. Node: N0: no regional lymph node metastasis; N1: metastasis in regional lymph nodes. Metastasis: M0: no distant metastasis; M1: distant metastasis present.

D. Prediction of Prostate Cancer Recurrence or Tumor Aggressiveness

A determination of disease recurrence and/or tumor aggressiveness can be made using copy number variation values (e.g., copy number aberration values) and clinical factor values. In some embodiments, the presence of specific diseased genomic regions or the number of diseased genomic regions (e.g., the GEMCaP biomarkers) can be factored into the prediction of recurrence risk or prediction of tumor aggressiveness. Each value assigned to each of the clinical factors (e.g., the CAPRA-S factors) can also be incorporated into this prediction. For instance, values assigned to the GEMCaP biomarkers and the CAPRA-S factors can be analyzed statistically as continuous and individual variables in a prediction. The use of both copy number variation values and the clinical factor values improves the performance of the prediction. A statistics-based prediction of prognostic indicators can be evaluated according to concordance statistics or a concordance index (C-index). For example, a prediction of prostate cancer risk based only on the copy number variations described herein using a specific threshold value (e.g., at least 20% of the genomic regions are scored as diseased) had a lower C-index of 0.6388, while the prediction that used both copy number variation and the clinical factors described herein had a C-index of 0.7554. A C-index of 0.7253 was obtained if only the clinical factors were used for predicting recurrence risk. These results show that predictions of risk of disease recurrence are statistically more robust when copy number variations at specific genomic regions such as those of GEMCaP and clinical factors such as those of CAPRA-S are used together.

The predictive model of recurrence risk can be refined upon performing a Cox proportional hazards modeling with the outcome variable being the time to recurrence and the predictors to be the genomic biomarkers of GEMCaP and the clinical factors (including PSA level) CAPRA-S. The modeling provides a predicted probability of recurrence for each patient in the cohort that is used to modify the model. As such, the modeling can provided information about which individual or combination of GEMCaP and CAPRA-S scores correspond to low or high risk of recurrence.

E. Data Analysis

Once the sample(s) from the human subject have been analyzed as described above, a value or index is generated for predicting likelihood of the presence or reoccurrence of prostate cancer. When two or more biomarkers (copy number and/or other biological biomarkers), clinical factors, or other criteria are used in the method described herein, the level of each biomarker and/or clinical factor can be weighted and combined. Thus, a test value may be provided by (a) weighting the determined level of each biomarker with a predefined coefficient, and (b) combining the weighted level to provide a test value. The combining step can be by straight addition or averaging (i.e., weighted equally), by a one or more predefined coefficients, or other statistical methods.

Once generated, the value from a sample can be compared to one or more threshold value(s) to provide a likelihood of the presence of reoccurrence of prostate cancer. In order to establish a threshold value for practicing the method, a reference population of subjects can be used. In some embodiments, a population of prostate cancer patients receiving treatment for prostate cancer (e.g., radical prostatectomy) can be used. In some embodiments, these patients are within the appropriate parameters, if applicable, for the purpose of screening for and/or monitoring cancer using the methods of the present disclosure. Optionally, the patients are of similar age or similar ethnic background. The status of the selected patients can be confirmed by well established, routinely employed methods including but not limited to general physical examination of the individuals and general review of their medical history.

Furthermore, the selected group of patients will generally be of sufficient size, such that the average value in the sample obtained from the group can be reasonably regarded as representative of a particular indication, for example indicative of reoccurrence of prostate cancer or not after a set period of time (e.g., five years) after treatment.

Once an average value is established based on the individual values found in each subject of the selected group, this average or median or representative value or profile can be used as a threshold value. For example, a sample value over the threshold value can indicate a more than average likelihood of reoccurrence of prostate cancer whereas a sample value below the threshold value can indicate an average or below-average likelihood of reoccurrence of prostate cancer. In some embodiments, a standard deviation is also determined during the same process. In some cases, separate threshold values may be established for separately defined groups having distinct characteristics such as age, gender, or ethnic background.

According to the methods described herein, the sample is compared to one or more reference or threshold values. In some embodiments, the sample value is deemed "high' if it is at least 1, 2, 3, 4, 5, 10, 15, 20 or more standard deviations greater than the reference value subjects. In other embodiments, the sample value is below the threshold if the sample value is at least 1, 2, 3, 4, 5, 10, 15, 20 or more standard deviations lower than the reference or threshold value.

In some embodiments, a computer-based analysis program is used to translate the raw data generated by the detection methods described herein (e.g., the presence, absence, or amount of a given marker or markers) into a score of predictive value to a clinician.

The score, as determined according to the methods above, can predict that the patient has an above-average likelihood of tumor recurrence. In some cases, the patient has a high risk of recurrence. The score can also predict that the patient has an average or below-average likelihood of tumor recurrence. In such instances, the patient can have a low or intermediate risk of recurrence.

F. Computer-Implemented Methods, System, and Device

Any of the methods described herein may be totally or partially performed with a computer system including one or more processors, which can be configured to perform the steps. Thus, embodiments are directed to computer systems configured to perform the steps of any of the methods described herein, potentially with different components performing a respective step or a respective group of steps. Although presented as numbered steps, steps of methods herein can be performed at a same time or in a different order. Additionally, portions of these steps may be used with portions of other steps from other methods. Also, all or portions of a step may be optional. Any of the steps of any of the methods can be performed with modules, circuits, or other means for performing these steps.

In some aspects of the present disclosure, a computer product is provided. The computer product can comprise a non-transitory computer readable medium storing a plurality of instructions that when executed determine a human subject's risk of prostate cancer recurrence. The instructions include receiving a set of determined copy numbers for a set of genomic regions or portions thereof comprising one or more genomic regions or portions thereof selected from the group consisting of human chromosome(s) 3q26.2, 3826.32, 3826.3, 5p15.1, 7p22.3, 7811.22, 7811.23, 7822.1, 7831.31, 9834.1, 11p15.4, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 and 16q23.1 in a biological sample from the subject; comparing the set of determined copy numbers to a set of reference copy numbers for the corresponding set of genomic regions or portions thereof; scoring each genomic region or portion thereof as diseased or normal, wherein the genomic region or portion thereof is diseased if there is an increase in copy number at the genomic region or portion thereof at human chromosome 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, or 22813.1 in the biological sample compared to the reference copy number, and if there is a decrease in copy number at the genomic region or portion thereof at human chromosome 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 or 16q23.1 in the biological sample compared to the reference copy number; comparing the number of genomic regions or portions thereof that are scored as diseased to a threshold value for disease recurrence to generate a copy number score; receiving a set of determined clinical factors for the subject, the set of determined clinical factors comprising one or more clinical factors comprising a PSA level (e.g., a preoperative PSA level or a postoperative PSA level), pathogenic Gleason score, surgical margin status, presence of extracapsular extension, presence of seminal vesicle, and presence of lymph node involvement to generate a clinical score; determining the subject's risk of prostate cancer recurrence by based on a calculation comprising the copy number score and the clinical score.

Any of the computer systems mentioned herein may utilize any suitable number of subsystems. Examples of such subsystems are shown in FIG. 1 in computer apparatus 100.

In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 1 are interconnected via a system bus 175. Additional subsystems such as a printer 174, keyboard 178, storage device(s) 179, monitor 176, which is coupled to display adapter 182, and others are shown. Peripherals and input/output (I/O) devices, which couple to I/O controller 171, can be connected to the computer system by any number of means known in the art, such as serial port 177. For example, serial port 177 or external interface 181 (e.g. Ethernet, Wi-Fi, etc.) can be used to connect computer system 100 to a wide area network such as the Internet, a mouse input device, or a scanner. The interconnection via system bus 175 allows the central processor 173 to communicate with each subsystem and to control the execution of instructions from system memory 172 or the storage device(s) 179 (e.g., a fixed disk, such as a hard drive or optical disk), as well as the exchange of information between subsystems. The system memory 172 and/or the storage device(s) 179 may embody a computer readable medium. Any of the data mentioned herein can be output from one component to another component and can be output to the user.

A computer system can include a plurality of the same components or subsystems, e.g., connected together by external interface 181 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present disclosure can be implemented in the form of control logic using hardware (e.g. an application specific integrated circuit or field programmable gate array) and/or using computer software with a generally programmable processor in a modular or integrated manner. As user herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments of the present disclosure using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

In another aspect of the present disclosure, a computer-implemented method for determining a risk of prostate cancer recurrence in a subject is provided. The computer-implemented method can include (a) receiving, at one or more computer system(s), information about a set of copy numbers for a set of genomic regions or portions thereof comprising one or more genomic regions or portions thereof selected from the group consisting of human chromosome(s) 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 and 16q23.1 in a biological sample obtained from the subject; (b) performing, with one or more processors associated with the computer system(s), a comparison of the set of copy numbers in the biological sample to a set of reference copy numbers to score the genomic region or portion thereof as diseased or normal, wherein the genomic region or portion thereof is diseased if there is an increase in copy number at the genomic region or portion thereof at human chromosome 3q26.2, 3q26.32, 3q26.3, 5p15.1, 7p22.3, 7811.22, 7811.23, 7822.1, 7831.31, 9834.1, 11p15.4, 17q21.33, 17825.3, or 22813.1 in the biological sample compared to the reference copy number, and if there is a decrease in copy number at the genomic region or portion thereof at human chromosome 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 or 16q23.1 in the biological sample compared to the reference copy number; (c) performing, with one or more processors associated with the computer system (s), a comparison of the number of genomic regions or portions thereof that are scored as diseased to a threshold value for disease recurrence to generate a copy number score; (d) receiving, at one or more computer system(s), information about a set of clinical factors for the subject, the set of clinical factors comprising one or more of the clinical factors comprising a PSA level (e.g., a preoperative PSA level), pathogenic Gleason score, surgical margin status, presence of extracapsular extension, presence of seminal vesicle, and presence of lymph node involvement, wherein each clinical factor is assigned a numerical value; (e) generating, with one or more processors associated with the computer system(s), a clinical score based on the numerical values assigned to the set of clinical factors; and (f) generating, with one or more processors associated with the computer system(s), a determination of a risk of prostate cancer recurrence comprising the copy number score and the clinical score, and predicting a high risk of prostate cancer recurrence if the risk of prostate cancer recurrence is higher than a threshold risk score, or a low risk of prostate cancer recurrence if the risk of prostate cancer recurrence is lower than the threshold risk score.

G. Kits

For use in diagnostic, and research applications described above, kits are also provided by the invention. The kits of the invention may comprise any or all of the reagents to perform the methods described herein. In the diagnostic and research applications such kits may include any or all of the following: assay reagents, buffers, nucleic acids that bind to at least one of the genomic regions or genes described herein, hybridization probes and/or primers, antibodies or other moieties that specifically bind to at least one of the polypeptides encoded by the genes described herein, etc. Additionally, an array such as a DNA microarray, an RNA microarray, a miRNA microarray, or an antibody array can be provided herein.

In addition, the kits may include instructional materials containing directions (i.e., protocols) for the practice of the methods provided herein. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

H. Selecting Therapeutic Measures

In some embodiments, the method of the present disclosure also includes selecting a therapeutic intervention for the subject having a risk (an above-average likelihood) of prostate cancer recurrence. A radiation therapy, chemotherapy, drug therapy, e.g., hormone therapy, immunotherapy, surgery, or any combination thereof can be selected. Non-limiting examples of drug therapies include abiraterone, bicalutamide, debarelix, enzalutamide, eflutamide, goserelin, histrelin, ketoconazole, leuprolide, mifepristone, nilutamide, prednisone and triptorelin. Without limitations, examples of chemotherapy drug include cabazitaxel, carboplatin, docetaxel, doxorubicin, estramustine, etoposide, mitoxantrone, paclitaxel, vinblastine, vinorelbine. Possible immunotherapies include sipuleucel-T (Provenge), ipilimumab, and bevacizumab. In some embodiments, one or more therapeutic interventions are recommended. Each therapy can be administered simultaneously or sequentially.

A treatment intervention can be selected or recommended for a patient with an above-average likelihood of tumor recurrence. The treatment can include administering to the patient a therapy, e.g., radiotherapy, chemotherapy, surgery, drug therapy, immunotherapy, and a combination thereof, that kills, inhibits, or removes prostate cancer cells. A disease management approach can be selected or recommended for a patient with an average or below-average likelihood of tumor recurrence. A disease management approach can include watchful waiting or active surveillance.

During watchful waiting for prostate cancer no treatment is provided. Periodic tests and assessments can be performed to monitor for changes to detect recurrence of the patient's prostate cancer. Useful disease management tests include a digital rectal exam (DRE), PSA blood test, transrectal ultrasound (TRUS), prostate biopsy, lymph node biopsy, bone scan, computed tomography (CT scan), magnetic resonance imaging (MRI), and the like. In some embodiments, watchful waiting includes include selecting one or more tests for monitoring prostate cancer.

III. EXAMPLES

The following examples are offered to illustrate, but not to limit, the claimed invention.

Example 1. Predicting Recurrence

Previously, we discovered a set of DNA-based biomarkers (copy number biomarkers) that predict prostate cancer recurrence after radical prostatectomy (RP) (Paris et al., Hum Mol Genet 13:1303-13, 2004) and had evaluated the marker set in UCSF patient sets (Paris et al., Clin Cancer Res 16:195-202, 2010; Paris et al., Int J Biol Markers 20:141-5, 2005). These DNA biomarkers map to 39 loci termed GEMCaP for Genomic Evaluators of Metastatic Prostate Cancer. One of these loci maps to a telomeric region (2qtel) and was dropped from future analysis involving the biomarker set. We previously defined a 'positive' GEMCaP result as an abnormal result for >20% of the 39 loci. We aimed to validate the GEMCaP assay in predicting recurrence after RP using an external (i.e., non-UCSF) cohort of patients who underwent RP for prostate cancer. We report the results from 140 patients, which includes 54 from the Cleveland Clinic and 86 from the University of Rochester Cancer Center. Median time to recurrence was 45.3 months and median follow-up time among those who did not recur was 120.2 months.

After adjusting for clinical site, a positive GEMCaP score was associated with a higher risk of biochemical recurrence (p=0.001). The goal of GEMCaP is to supplement current risk prediction models that only use clinical variables (inclusive of PSA), such as CAPRA-S(Cooperberg et al., Cancer, 117:5039-45, 2011). The concordance index (C-index; a predictive measure of how well a model distinguishes between individuals with and without the outcome of interest) improved when including GEMCaP (GEMCaP with a threshold of >20% abnormal) and CAPRA-S into the same model (0.7554 compared to 0.6388 (GEMCaP alone) and 0.7253 (CAPRA-S alone)).

Merely adding GEMCaP to CAPRA-S (both as continuous variables) was not as predictive as including both in the same model (0.6872 vs 0.7487). This latter result suggests that using an algorithm for GEMCaP score determination is ideal when creating an overall recurrence risk score that includes CAPRA-S.

The predictive model of recurrence risk can be modified upon running a Cox proportional hazards model with time to recurrence as the outcome variable and with GEMCaP and CAPRA-S as predictors. The modeling provides a predicted probability of recurrence for each patient in the cohort that is used to refine the model. As such, these predictions can inform which GEMCaP and CAPRA-S scores correspond to low or high risk of recurrence.

Example 2. Distinguishing Aggressive and Indolent Prostate Cancers

Methods

Men were identified at University California San Francisco (UCSF) and University of Washington (UW) with low-risk cancers defined by biopsy Gleason score ≤3+3, PSA≤10 ng/ml, and clinical stage ≤T2 who underwent immediate prostatectomy. Formalin fixed and paraffin-embedded (FFPE) prostate tissue from 381 cases (UCSF) 260 cases (UW). Tumor tissue was macrodissected and DNA was extracted and analyzed for the GEMCaP copy number variation score, and RNA was extracted and analyzed for the cell cycle progression (CCP) score, both well-validated and previously reported scores. Pathologic outcomes were identified as minor upgrading/upstaging (UGUS) (pGS (pathological Gleason score) 3+4 or pT3a) or major UGUS (pGS≥4+3 or ≥pT3b), and multinomial regression was performed to determine GEMCaP's ability to predict these outcomes, controlling for PSA, percent of biopsy cores positive, age, and clinical site.

Results

Overall, 357 men had no UGUS event at prostatectomy, 236 had a minor event, and 67 had a major event. GEMCaP was directly associated with extent of UGUS on univariate analysis (p<0.01). On multivariable analysis, GEMCaP predicted minor UGUS (OR 1.09, 95% CI 1.05-1.12) and major UGUS (OR 1.06, 95% CI 1.04-1.09). The other clinical parameters were not significant in this model.

Thus, biomarker signatures based on the analysis of DNA independently predicted adverse pathology among men with clinically low-risk prostate cancer undergoing prostatectomy.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A method for evaluating a biopsy sample to determine a likelihood that a prostate tumor will be aggressive:
   (a) detecting copy numbers for a set of genomic regions or portions thereof in a nucleic acid sample from a biopsy obtained from a human patient that has a prostate tumor having a Gleason score ≤3+3 and clinical stage ≤T2, wherein the set of genomic regions or portions thereof comprises genomic regions or portions thereof at human chromosomes 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 and 16q23.1; and
   wherein the genomic region or portion thereof at human chromosome 3q26.2 comprises a genomic region or portion thereof at chr3:168805847-168806351, the genomic region or portion thereof at human chromosome 3q26.32 comprises a genomic region or portion thereof at chr3:177272862-177430308, the genomic region or portion thereof at human chromosome 3q26.3 comprises a genomic region or portion thereof at chr3: 178951957-178952231, the genomic region or portion thereof at human chromosome 5p15.1 comprises a genomic region or portion thereof at chr5:17412420-17592769, the genomic region or portion thereof at human chromosome 7p22.3 comprises a genomic region or portion thereof at chr7:1062717-1063110 or chr7:2396631-2396986, the genomic region or portion thereof at human chromosome 7q11.22 comprises a genomic region or portion thereof at chr7:69577003-69759243, the genomic region or portion thereof at human chromosome 7q11.23 comprises a genomic region or portion thereof at chr7:73442517-73483030, the genomic region or portion thereof at human chromosome 7q22.1 comprises a genomic region or portion thereof at chr7:100705095-100899914, the genomic region or portion thereof at human chromosome 7q31.31 comprises a genomic region or portion thereof at chr7:117432355-117432817, the genomic region or portion thereof at human chromosome 9q34.1 comprises a genomic region or portion thereof at chr9: 132262446-132370055, the genomic region or portion thereof at human chromosome 11p15.4 comprises a genomic region or portion thereof at chr11:2904813-2907001, 17q21.33 comprises a genomic region or portion thereof at chr17:47454237-47654582, the genomic region or portion thereof at human chromosome 17q25.3 comprises a genomic region or portion thereof at chr17:77702278-77862768, the genomic region or portion thereof at human chromosome 22q13.1 comprises a genomic region or portion thereof at chr22:39620241-39631867, the genomic region or portion thereof at human chromosome 4p13 comprises a genomic region or portion thereof at chr4:44558370-44559188, the genomic region or portion thereof at human chromosome 5q13.1 comprises a genomic region or portion thereof at chr5:67803220-67803609, the genomic region or portion thereof at human chromosome 5q14.3 comprises a genomic region or portion thereof at chr5:85936281-86082787, the genomic region or portion thereof at human chromosome 5q21.1 comprises a genomic region or portion thereof at chr5: 102652546-102813426, the genomic region or portion thereof at human chromosome 5q21.2 comprises a genomic region or portion thereof at chr5:103047961-103230737, the genomic region or portion thereof at human chromosome 5q21.3 comprises a genomic region or portion thereof at chr5:108476063-108523316, the genomic region or portion thereof at human chromosome 5q23.1 comprises a genomic region or portion thereof at chr5:116987516-116987850, at the genomic region or portion thereof of human chromosome 6q14.1 comprises a genomic region or portion thereof at chr6:79240539-79417494, the genomic region or portion thereof at human chromosome 6q21 comprises a genomic region or portion thereof at chr6:105514625-105687735, the genomic region or portion thereof at human chromosome 6q21 comprises a genomic region or portion thereof at chr6: 112401839-112550863, the genomic region or portion thereof at human chromosome 8p22 comprises a genomic region or portion thereof at chr8:15649576-15649945, the genomic region or portion thereof at human chromosome 8p21.2 comprises a genomic region or portion thereof at chr8:25189716-25280826, the genomic region or portion thereof at human chromosome 8p21.2 comprises a genomic region or portion thereof at chr8:26260492-26362544, the genomic region or portion thereof at human chromosome 8p21.2 comprises a genomic region or portion thereof at chr8: 26555762-26676439, the genomic region or portion thereof at human chromosome 8p12 comprises a genomic region or portion thereof at chr8:32412399-32572832, the genomic region or portion thereof at human chromosome 10q23.31 comprises a genomic region or portion thereof at chr10:89991491-90075908, the genomic region or portion thereof at human chromosome 13q14.11 comprises a genomic region or portion thereof at chr13:40129477-40205232, the genomic region or portion thereof at human chromosome 13q14.11 comprises a genomic region or portion thereof at chr13:41044273-41044745, the genomic region or portion thereof at human chromosome 13q14.11 comprises a genomic region or portion thereof at chr13:43679675-43868415, the genomic region or portion thereof at human chromosome 13q14.13 comprises a genomic region or portion thereof at chr13:45857696-45858096, the genomic region or portion thereof at human chromosome 13q14.2 comprises a genomic region or portion thereof at chr13:49015662-49140264, the genomic region or portion thereof at human chromosome 13q14.3 comprises a genomic region or portion thereof at chr13: 51245126-51245378 and the genomic region or portion thereof at human chromosome 16q23.1 comprises a genomic region or portion thereof at chr16:77158148-77311367;

(b) scoring each genomic region or portion thereof as diseased or normal to generate a copy number score, wherein the scoring is determined based on the copy number in the nucleic acid sample from the biopsy compared to a normal reference copy number of non-cancerous tissue; and the genomic region or portion thereof is scored as diseased if there is an increase in copy number at the genomic region or portion thereof located at human chromosome 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, or 22q13.1 in the nucleic acid sample from the biopsy compared to the reference copy number, and if there is a decrease in copy number at the genomic region or portion thereof located at human chromosome 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 or 16q23.1 in the nucleic acid sample from the biopsy compared to reference copy number;

(c) predicting an increased risk of aggressiveness of the prostate tumor when at least 20% of the genomic regions are scored as diseased; and (d) treating a patient that is predicted to have an increased risk of aggressiveness of the prostate tumor in (c) with a therapy to kill, inhibit, or remove prostate cancer cells.

2. The method of claim 1, wherein the patient has not received a therapy to treat the prostate tumor.

3. The method of claim 1, where the patient has a PSA level of ≤10 ng/ml.

4. The method of claim 1, further comprising calculating a clinical score based on at least one clinical factor selected from the group consisting of clinical stage, Gleason score, and PSA level.

5. The method of claim 1, wherein detecting the set of copy numbers comprises performing comparative genomic hybridization, genomic sequencing, or a genomic amplification reaction assay.

6. A method of treating a human patient that has a prostate tumor having a Gleason score ≤3+3 and clinical stage ≤T2, the method comprising:

(a) determining that the human patient has an increased likelihood of having an aggressive prostate tumor by obtaining or having obtained a nucleic acid sample from a biopsy of the prostate tumor;

detecting or having detected copy number changes in a set of genomic regions or portions thereof in the nucleic acid sample, wherein the set of genomic regions or portions thereof comprises genomic regions or portions thereof at human chromosomes 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, 22q13.1, 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 and 16q23.1; and wherein the genomic region or portion thereof at human chromosome 3q26.2 comprises a genomic region or portion thereof at chr3:168805847-168806351, the genomic region or portion thereof at human chromosome 3q26.32 comprises a genomic region or portion thereof at chr3:177272862-177430308, the genomic region or portion thereof at human chromosome 3q26.3 comprises a genomic region or portion thereof at chr3:178951957-178952231, the genomic region or portion thereof at human chromosome 5p15.1 comprises a genomic region or portion thereof at chr5:17412420-17592769, the genomic region or portion thereof at human chromosome 7p22.3 comprises a genomic region or portion thereof at chr7:1062717-1063110 or chr7:2396631-2396986, the genomic region or portion thereof at human chromosome 7q11.22 comprises a genomic region or portion thereof at chr7:69577003-69759243, the genomic region or portion thereof at human chromosome 7q11.23 comprises a genomic region or portion thereof at chr7:73442517-73483030, the genomic region or portion thereof at human chromosome 7q22.1 comprises a genomic region or portion thereof at chr7:100705095-100899914, the genomic region or portion thereof at human chromosome 7q31.31 comprises a genomic region or portion thereof at chr7:117432355-117432817, the genomic region or portion thereof at human chromosome 9q34.1 comprises a genomic region or portion thereof at chr9:132262446-132370055, the genomic region or portion thereof at human chromosome 11p15.4 comprises a genomic region or portion thereof at chr11:2904813-2907001, 17q21.33 comprises a genomic region or portion thereof at chr17:47454237-47654582, the genomic region or portion thereof at human chromosome 17q25.3 comprises a genomic region or portion thereof at chr17:77702278-77862768, the genomic region or portion thereof at human chromosome 22q13.1 comprises a genomic region or portion thereof at chr22:39620241-39631867, the genomic region or portion thereof at human chromosome 4p13 comprises a genomic region or portion thereof at chr4:44558370-44559188, the genomic region or portion thereof at human chromosome 5q13.1 comprises a genomic region or portion thereof at chr5:67803220-67803609, the genomic region or portion thereof at human chromosome 5q14.3 comprises a genomic region or portion thereof at chr5:85936281-86082787, the genomic region or portion thereof at human chromosome 5q21.1 comprises a genomic region or portion thereof at chr5:102652546-102813426, the genomic region or portion thereof at human chromosome 5q21.2 comprises a genomic region or portion thereof at chr5:103047961-103230737, the genomic region or portion thereof at human chromosome 5q21.3 comprises a genomic region or portion thereof at chr5:108476063-108523316, the genomic region or portion thereof at human chromosome 5q23.1 comprises a genomic region or portion thereof at chr5:116987516-116987850, at the genomic region or portion thereof of human chromosome 6q14.1 comprises a genomic region or portion thereof at chr6:79240539-79417494, the genomic region or portion thereof at human chromosome 6q21 comprises a genomic region or portion thereof at chr6:105514625-105687735, the genomic region or portion thereof at human chromosome 6q21 comprises a genomic region or portion thereof at chr6:112401839-112550863, the genomic region or portion thereof at human chromosome 8p22 comprises a genomic region or portion thereof at chr8:15649576-15649945, the genomic region or portion thereof at human chromosome 8p21.2 comprises a genomic region or portion thereof at chr8:25189716-25280826, the genomic region or portion thereof at human chromosome 8p21.2 comprises a genomic region or portion thereof at chr8:26260492-26362544, the genomic region or portion thereof at human chromosome 8p21.2 comprises a genomic region or portion thereof at chr8:26555762-26676439, the genomic region or portion thereof at human chromosome 8p12 comprises a genomic region or portion thereof at chr8:32412399-32572832, the genomic region or portion thereof at human chromosome 10q23.31 comprises a genomic region or portion thereof at chr10:89991491-90075908, the genomic region or portion thereof at human chromosome 13q14.11 comprises a genomic region or portion thereof at chr13:40129477-40205232, the genomic region or portion thereof at human chromosome 13q14.11 comprises a genomic region or portion thereof at chr13:41044273-41044745, the genomic region or portion thereof at human chromosome 13q14.11 comprises a genomic region or portion thereof at chr13:43679675-43868415, the genomic region or portion thereof at human chromosome 13q14.13 comprises a genomic region or portion thereof at chr13:45857696-45858096, the genomic region or portion thereof at human chromosome 13q14.2 comprises a genomic region or portion thereof at chr13:49015662-49140264, the genomic region or portion thereof at human chromosome 13q14.3 comprises a genomic region or portion thereof at chr13:51245126-51245378 and the genomic region or portion thereof at human chromosome 16q23.1 comprises a genomic region or portion thereof at chr16:77158148-77311367;

scoring or having scored each genomic region or portion thereof as diseased or normal to generate a copy number score, wherein the scoring is determined based on the copy number in the nucleic acid sample from the biopsy compared to a normal reference copy number of noncancerous tissue; and the genomic region or portion thereof is scored as diseased if there is an increase in copy number at the genomic region or portion thereof located at human chromosome 3q26.2, 3q26.32, 3q26.3, 5p15.1, 7p22.3, 7q11.22, 7q11.23, 7q22.1, 7q31.31, 9q34.1, 11p15.4, 17q21.33, 17q25.3, or 22q13.1 in the nucleic acid sample from the biopsy compared to the reference copy number, and if there is a decrease in copy number at the genomic region or portion thereof located at human chromosome 4p13, 5q13.1, 5q14.3, 5q21.1, 5q21.2, 5q21.3, 5q23.1, 6q14.1, 6q21, 8p22, 8p21.2, 8p12, 10q23.31, 13q14.11, 13q14.13, 13q14.2, 13q14.3 or 16q23.1 in the nucleic acid sample from the biopsy compared to reference copy number;

(b) identifying that the human patient has at least 20% of the genomic regions in the nucleic acid sample scored as diseased and then administering a therapy to kill, inhibit, or remove prostate cancer cells.

7. The method of claim 6, where the patient has a PSA level of ≤10 ng/ml.

8. The method of claim 6, further comprising calculating a clinical score based on at least one clinical factor selected from the group consisting of clinical stage, Gleason score, and PSA level.

* * * * *